(12) United States Patent
Moriarty

(10) Patent No.: US 7,623,971 B2
(45) Date of Patent: Nov. 24, 2009

(54) METHOD, SYSTEM AND COMPUTER PROGRAM PRODUCT FOR TECHNICAL MANAGEMENT AND BIOCONTROL OF DISEASE IN ANIMAL PRODUCTION SYSTEMS

(75) Inventor: David J. W. Moriarty, Wellington Point (AU)

(73) Assignee: Acuabiotec LLC, Potomac, MD (US)

( * ) Notice: Subject to any disclaimer, the term of this patent is extended or adjusted under 35 U.S.C. 154(b) by 1085 days.

(21) Appl. No.: 10/381,271

(22) PCT Filed: Sep. 25, 2001
(Under 37 CFR 1.47)

(86) PCT No.: PCT/US01/27731

§ 371 (c)(1),
(2), (4) Date: Sep. 8, 2003

(87) PCT Pub. No.: WO02/27995

PCT Pub. Date: Apr. 4, 2002

(65) Prior Publication Data

US 2004/0126365 A1  Jul. 1, 2004

Related U.S. Application Data

(60) Provisional application No. 60/234,784, filed on Sep. 25, 2000.

(51) Int. Cl.
*G06F 19/00* (2006.01)
*A61K 39/07* (2006.01)

(52) U.S. Cl. ........................... 702/19; 424/246.1
(58) Field of Classification Search ................. None
See application file for complete search history.

(56) References Cited

U.S. PATENT DOCUMENTS

| | | | |
|---|---|---|---|
| 4,211,183 A | 7/1980 | Hoult | |
| 5,353,745 A | 10/1994 | Fahs | |
| 6,033,559 A | 3/2000 | Bender et al. | |
| 6,432,698 B1 | 8/2002 | Gaugler et al. | |

FOREIGN PATENT DOCUMENTS

| AU | 199665750 B2 | 5/2000 |
|---|---|---|

OTHER PUBLICATIONS

Gildberg et al. (Aquaculture (1998) vol. 167; pp. 103-113).*
Moriarty (Sustainable Aquaculture; INFOFISH, Kuala Lampur, Malaysia (1997); pp. 115-121).*
Paul Williams; "Targeting Virulence as a Means of Attenuating Infection"; Journal of Pharmacy and Pharmacology, London, GB, vol. Suppl. No. 52; Sep. 10, 2000; p. 71; XP-001079747.
Fowler, P., A Methodology for the Design of Complex Computer Systems in Agriculture and Aquaculture, UMI Dissertation Services, p. 1-125, 1998—University of Florida correction to date LAC Jul. 2, 2009.
Lee, P., Process Control and Artificial Intelligence Software for Aquaculture, Aquaculture Engineering, 2000, vol. 23, pp. 13-36.
Ernst et al., AquaFarm, Aquaculture Engineering. 2000, vol. 23, p. 121-179.
Moriarty, David J., Disease Control in Shrimp Aquaculture with Probiotic Bacteria, Microbial Interactions in Aquaculture, 1999, pp. 1-7.
Dierick-Koenen et al., Optimization of an Antibiotic Residue Screening Test, Base on Inhibition of *Bacillus* Subtilis BGA, with Experimental Design, Food Addictives and Contaminants, 1998, vol. 15, No. 5, pp. 528-534.
Hovance World Wide Web Search on Yahoo (www.marinelabs.com) Nitrospira: The real nitrate-oxidizing bacteria in aquaria, Aquarium Frontiers, Mar. 1998.

* cited by examiner

*Primary Examiner*—Lori A Clow
(74) *Attorney, Agent, or Firm*—Carlos R. Villamar; Roberts Mlotkowski Safran & Cole P.C.

(57) ABSTRACT

A system, method and computer program product for controlling disease at an end user location, including (a) testing a range of candidates including at least one of: (i) *Bacillus* species, (i) *Bacillus* strains, (iii) species of beneficial bacteria (iv) strains of beneficial bacteria and (v) strains of beneficial bacterial viruses, against samples including at least one of pathogenic *Vibrio*, Gram negative pathogenic bacteria and Gram positive pathogenic bacteria taken from an end user location; (b) performing at least one of the following steps: (i) selecting one or more of the candidates that one of inhibit and attack at least one of the samples by direct inhibition of at least one of in situ antibiotic production, competitive exclusion, production of enzymes that degrade quorum sensing molecules, and (ii) testing a range of quorum sensing inhibitor compounds against the samples; and (c) performing the steps (a) and (b) for the end user location, including one of a country, major region and individual end user location, to target microbial technology to use in bio-control of disease specific to the end user location.

12 Claims, 10 Drawing Sheets

METHOD, SYSTEM AND COMPUTER PROGRAM PRODUCT FOR TECHNICAL MANAGEMENT AND BIOCONTROL OF DISEASE IN ANIMAL PRODUCTION SYSTEMS

CROSS REFERENCE TO RELATED CASES

The present invention claims the benefit of priority under 35 U.S.C. § 119(e) to U.S. Provisional Patent Application Ser. No. 60/0234,784 of Villamar et al., entitled "METHOD, SYSTEM AND COMPUTER PROGRAM PRODUCT FOR TECHNICAL MANAGEMENT AND BIOCONTROL OF DISEASE OF AQUATIC ANIMALS," filed on Sep. 25, 2000 and is related to U.S. Provisional Patent Application Ser. No. 60/213,538 of Villamar et al, entitled "BIOACTIVE FOOD COMPLEX METHOD FOR MAKING BIOACTIVE FOOD COMPLEX PRODUCT AND METHOD FOR CONTROLLING DISEASE," filed on Jun. 23, 2000 and PCT Application Ser. No. PCT/US/16489 of Villamar et al, entitled "BIOACTIVE FOOD COMPLEX, METHOD FOR MAKING BIOACTIVE FOOD COMPLEX PRODUCT AND METHOD FOR CONTROLLING DISEASE," filed on 22 Jun. 2001, the entire contents of all of which are incorporated by reference herein.

BACKGROUND OF THE INVENTION

1. Field of the Invention

The present invention generally relates to the field of biocontrol of disease in animal production systems and more specifically to a method, system and computer program product for the technical management and biocontrol of disease in animal production systems by use of microbial biotechnology. The present invention includes use of various technologies described in the references identified in the appended LIST OF REFERENCES and/or cross-referenced throughout the specification by numerals in brackets corresponding to the respective references, the entire contents of all of which are incorporated herein by reference.

2. Discussion of the Background

Aquatic farming is the fastest growing sector of international agribusiness today (estimated farm gate value over US$30 billion/yr), with double-digit growth in major geographic regions where fish and shrimp are grown commercially. Sustained growth in aquaculture is needed to compensate for declining traditional fisheries and to meet a growing demand for high-value protein. Harvests of marine and freshwater finfish and shellfish for human consumption (herein defined as seafood) from the world's capture fisheries has been relatively stagnant at about 60 million tonne/yr over the last several years. During this time, major commercial fishing grounds have been classified as "Fully Exploited" or "Over Exploited." The Food and Agriculture Association (FAO) estimates world annual demand for seafood in the year 2010 at 110 to 120 million tonne. Best-case projections show a world supply of about 114 million tonne with less-favorable estimates at about 74 million tonne. A realistic scenario shows a deficit of 36 million to 46 million tonne. [1] Based on FAO and other estimates, about 10 million tonne of aquafeed will be used in the world in 1999 to feed the cultured of fish and shrimp.

At the same time, all segments of the aquaculture industry, e.g., shrimp, finfish, shellfish, etc., are being strongly affected by disease, especially bacterial diseases. Farmed shrimp production, which reached 737,200 tonne live weight in 1998 with an estimated trade value of about US$6 billion, is the most valuable export aquaculture crop and the hardest hit by disease in terms of financial losses to the industry. About 80% of the world's shrimp production takes place in Asia, the rest predominantly in Latin America. Thailand has been the world's largest farmed shrimp producer with over 210 000 tonne/yr and Ecuador was second with over 130,000 tonne; the production in both countries have been significantly affected by disease.

The damage caused by bacterial and viral diseases to the shrimp industry has been in the billions of dollars. Pathogenic *Vibrio* bacteria and viruses, such as Yellow Head Virus, White Spot (WSV) and Taura Virus have been among the most damaging pathogens. Central America was hit hard in 1999 by WSV and pathogenic *Vibrio* disease, causing great losses in production, for example, up to 50% in some countries. WSV can result in 100% mortality within the first few weeks after stocking shrimp ponds. Ecuador, the largest shrimp producing country in the Western Hemisphere was severely affected by WSV in 1999 and is estimated to have lost more than 40% of its annual production with no signs of significant recovery to date.

Chemicals and heavy use of antibiotics are the most commonly used methods to control shrimp diseases. However, these processes can be ineffective and dangerous. Indiscriminate use of antibiotics and disinfectants has led to an increase in bacteria having multiple antibiotic resistances. Many of the pathogens appear to have mutated to more virulent forms than were present a decade ago, resulting in greater rates of shrimp mortality. Thus, the incidence of the disease has been exacerbated by the actions of the shrimp farmers themselves using antibiotics.

Use of most chemicals and drugs is prohibited in the United States shrimp farming, wherein shrimp imports are tested for chemical residues and U.S. authorities have rejected shipments. Furthermore, the concern of potential transfer of antibiotic resistance to human pathogens and the negative marketing image created by use of chemicals and drugs can slow the growth and damage the aquaculture industry in the long-term.

The major disease agents around the world in aquaculture are bacteria, especially *Vibrio* species in marine systems. Often, a combination of viral and bacterial disease appears to be a widespread cause of mortality. For example, shrimp exposed to heavy environmental stress can be severely weakened by *Vibrio* sp. favoring invasion and increasing pathogenicity by virus, such as WSV. Conversely, shrimp that are infected by virus, but normally tolerate its pathogenicity can succumb to the virus with the additional stress of *Vibrio* infection.

Currently, pharmaceutical companies sell antibiotics to aquatic farmers. In addition, it is quite likely that problems have been exacerbated by the use of other antimicrobial compounds. Chlorine is widely used in hatcheries and ponds, but its use stimulates the development of multiple antibiotic resistance genes in bacteria [28, 29]. If antibiotics are used to kill bacteria, there are always some bacteria that survive, either strains of the pathogen or others, because they carry genes for resistance. These will then grow rapidly because their competitors are removed. Virulent pathogens that then re-enter the tank, perhaps from within biofilms in water pipes or in the guts of animals, can then exchange genetic information with the resistant bacteria and survive further doses of antibiotic. Thus, antibiotic-resistant strains of pathogens evolve rapidly [35].

The transfer of resistance to human pathogens and gut bacteria is of major concern. Such transfers probably happen easily and often. A gene coding for tetracycline resistance has been transferred between Prevotella, bacteria that normally live in the rumen of farm animals, and Bacteriodes, bacteria that normally live in human guts [30]. Resistance plasmids (R plasmids) encoding for many antibiotic resistance genes were transferred between pathogenic and non-pathogenic Gram negative bacteria in several environments including sea water [31]. In the presence of tetracycline concentrations that were not high enough to kill the bacteria, the rate of gene transfer between *Vibrio cholerae* and *Aeromonas salmonicida* increased 100 times.

This work raises questions not only about the use of antibiotics in aquaculture, but about the use of bacteria closely related to pathogenic species as probiotics. Not only antimicrobial resistance genes, but also genes for virulence can be transferred by R plasmids and transposons [32]. As the R plasmids can transfer genes between widely different bacteria in the Gram negative group, it would be potentially dangerous to use *Vibrio* or *Pseudomonas*, for example, as probiotics. However, the use of such bacteria is promoted, particularly *Vibrio alginolyticus* [33]. Based on observations by the present inventors, it is noted that the efficacy of *Vibrio* species as probiotics is short lived. Indeed, strains of *Vibrio alginolyticus* have been reported as virulent pathogens of shrimp larvae [34].

Throughout Asia, prawn farmers use antibiotics in large quantities. Warehouses supplying the industry in all the major centers sell a range of antibiotics in containers of 500 g or more in size. The antibiotics in current use include fluoroquinolones especially norfloxacin and enrofloxacin, furazolidone, oxolinic acid, oxytetracycline, trimethoprim and sulphadiazine. It is difficult to find out just how much antibiotic use there is in the industry, but it is possible to make an estimate from feed usage and production. In 1994, Thailand produced about 250,000 tonnes (a quarter of the world production) of farmed prawns, which consumed about 500,000-600,000 tonnes of feed. With the disease problems, prawn production has dropped to as low as 150,000 tonnes. For each crop at semi-intensive to intensive scales of production, farmers use 5-10 g antibiotics per kg feed at least once per day at weekly intervals; some use them for more extensive periods. Thus, as antibiotics would be used in about 10% of feed, the antibiotic usage in prawn farm production Thailand alone would be about 300-600 tonnes per year. And this does not include that used in hatcheries for fry production. As much of this will end up producing bacteria with multiple antibiotic resistance in farm effluents that then contaminate coastal waters, the potential impact on human health is significant [32, 35].

The overall strengths of antibiotics in the market place are long-term conditioning of individuals to the value of antibiotics for human and animal therapy; strong and well-financed marketing, and immediate short-term benefit. In most cases, the farmer does not see the long-term resistance build up and increased virulence until too late. Although some aquaculture producers are now realizing that they must move away from antibiotics, there are many who still use antibiotics. Antibiotics are recognized for their serious contribution to the collapse or decline of the shrimp industries in Taiwan, China, India, Thailand, and Philippines.

The use of probiotics to fight disease can be much more effective than use of antibiotics. The term "probiotic" was coined in the 1970s as a contrast to antibiotic and refers to beneficial bacteria found in the stomachs and intestines of animals that aid the animal in digestion and in fighting hazardous, disease-causing bacteria That is, when beneficial bacteria that are normal internal residents of the animal are added in larger numbers than present naturally, they promote health of the animal, in other words, they help the animal fight disease organisms. The probiotic approach to fighting disease does not share the above-noted disadvantages of an antibiotic approach. However, simply adding beneficial bacteria to aquaculture systems typically does not necessarily provide a solution to disease.

Among the companies attempting to combat disease in aquaculture are fermentation companies that manufacture or sell microbial products for industries other than aquaculture. However, fermentation companies and/or their marketers typically do not understand aquatic microbial ecology and aquaculture. These companies typically sell products that are inappropriate, ineffective and/or too expensive for aquatic farmers.

There are several dozen companies around the world selling bacteria referred to as "probiotics," although in most cases, the bacteria they sell do not meet the definition or function of probiotics, and indeed some are pathogens. Many companies are now selling *Lactobacillus* bacteria for fighting disease in shrimp aquaculture, but *Lactobacillus* is a probiotic for terrestrial animals and is the wrong bacterium for seawater and crustaceans. In many cases the microbial products may be suitable for wastewater treatment and bioremediation, but are not appropriate for disease control in aquaculture i.e., the bacteria do not have the genetic or molecular capacity to prevent disease. Most commercial products have very low concentrations of bacteria making them ineffective when added to large water volumes in aquaculture containment systems such as grow-out ponds. Some commercial companies have attempted to overcome the problem of low bacterial concentrations by requiring on-site fermentation by customers to generate sufficient numbers of bacteria to add to the large quantities of water in aquaculture containment systems.

An exemplary background art system of FIG. 10 includes a technology deployer 1002, a manufacturer 1004, a distributor 1006 and end users 1008 to 1010. In FIG. 10, the technology deployer 1002 determines bacteria 1038 that are perceived to have beneficial properties based presumably on scientific literature or based on their experience and on their ability to manufacture 1004 the bacteria 1038 in low concentration form by commercial fermentation methods. The distributor 1006, and /or the manufacturer 1004 in the case where sales are direct, then sells these bacteria 1038 to the end users 1008 to 1010. The more advanced technology deployers may perform bioassays in their labs to test the ability of their bacterial strains, which they are able to produce commercially, to inhibit generic pathogens, but typically do not test against strains selected from individual end user 1008 to 1010 locations. In some cases, the product 1038 must be further fermented in media by the end users 1008 to 1010 to increase the number of microbes before application at the end user 1008 to 1010 locations.

The above solutions are not effective in disease prevention and do not offer biocontrol of disease in aquaculture systems due to: (i) poor understanding of the physical, chemical and biological factors that affect disease control in commercial aquaculture systems, (ii) lack of technical support at the end user location (iii) lack of management of information generated by end user and its timely linkage to deployment of an appropriate technological response to epizootic conditions (iv) microbial products that do not prevent disease in commercial aquaculture systems, (v) microbial products that are not cost effective, and (vi) microbial products that are not user-friendly.

SUMMARY OF THE INVENTION

Accordingly, an object of this invention is to provide a novel method, system and computer program product for deploying effective control of disease in aquatic and terrestrial animal production systems including integration of technical and economic factors of such animal production systems with application of appropriate microbial technology to manage and prevent disease in such animal production systems.

Another object of this invention is to provide a novel method, system and computer program product for providing technology and know-how to help prevent or control production losses to White Spot Virus, *Vibrio* and other bacterial diseases affecting commercial shrimp farming.

Another object of this invention is to provide a novel method, system and computer program product for commercial application of microbial biotechnology and quorum sensing molecule inhibitors to help prevent or control losses to diseases affecting commercial shrimp farming, finfish and mollusc industries and retail aquarium sectors.

Another object of this invention is to provide a novel method, system and computer program product for providing products containing highly concentrated bacteria and/or quorum sensing molecule inhibitors, based on collection of appropriate data at end-user locations, analysis of the collected data, synthesis of biotechnology solutions and appropriate application programs and timely deployment of thereof.

Another object of this invention is to provide a novel method, system and computer program product for providing products containing highly concentrated bacteria and/or quorum sensing molecule inhibitors, based on data collected using biosensors, based on DNA probes targeting genes for virulence in bacteria and genes for identifying typical pathogenic bacteria.

Another object of this invention is to provide a novel method, system and computer program product for providing products containing highly concentrated bacteria and/or quorum sensing molecule inhibitors, which are safe, non-regulated, environmentally friendly bacterial isolates from nature.

Another object of this invention is to provide a novel method, system and computer program product for providing products containing highly concentrated bacteria and/or quorum sensing molecule inhibitors, which allow an aquatic farmer to employ effective bio-control of diseases and avoid use of harmful antibiotics and other drugs and chemicals, helping to remove these from the human food chain.

Another object of this invention is to provide a novel method, system and computer program product for providing products containing highly concentrated bacteria and/or quorum sensing molecule inhibitors, which help make shrimp farming "green" and sustainable.

Another object of this invention is to provide a novel method, system and computer program product for providing products containing highly concentrated bacteria and/or quorum sensing molecule inhibitors for maintaining health of aquatic species, including food finfish, shellfish (oysters, clams) and ornamental species in the retail aquarium trade.

Another object of this invention is to provide a novel method, system and computer program product for providing products containing highly concentrated bacteria and/or quorum sensing molecule inhibitors, which are ecologically and fight diseases that affect health of aquatic species, including food finfish, shellfish (oysters, clams, abalone etc.) and ornamental species in the retail aquarium trade.

Another object of this invention is to provide a novel method, system and computer program product for providing products containing highly concentrated bacteria and/or quorum sensing molecule inhibitors, which are carried "inside" an animal feed and are delivered via animal feeds, fertilizers and other products used in aquaculture.

Another object of this invention is to provide a novel method, system and computer program product providing products containing highly concentrated bacteria and/or quorum sensing molecule inhibitors, which are exported to distributors as concentrates, which are then blended with appropriate carriers for re-sale and/or direct farm use.

The above and other objects are achieved according to the present invention by providing a novel system, method and computer program product for controlling disease at an end user location, including (a) testing a range of candidates including at least one of: (i) *Bacillus* species, (i) *Bacillus* strains, (iii) species of beneficial bacteria (iv) strains of beneficial bacteria and (v) strains of beneficial bacterial viruses, against samples including at least one of pathogenic *Vibrio*, Gram negative pathogenic bacteria and Gram positive pathogenic bacteria taken from an end user location; (b) performing at least one of the following steps: (i) selecting one or more of the candidates that one of inhibit and attack at least one of the samples by direct inhibition of at least one of in situ antibiotic production, competitive exclusion, production of enzymes that degrade quorum sensing molecules, and (ii) testing a range of quorum sensing inhibitor compounds against the samples; and (c) performing the steps (a) and (b) for the end user location, including one of a country, major region and individual end user location, to target microbial technology to use in bio-control of disease specific to the end user location.

In another aspect of the present invention there is provided a novel apparatus and method for delivering microbes in an aquarium, including delivering the microbes in the aquarium via a device; and configuring the microbes to maintain a healthy microbial flora of the aquarium and of animals residing in the aquarium, to help prevent disease in the animals residing in the aquarium and to help maintain the aquarium clean.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
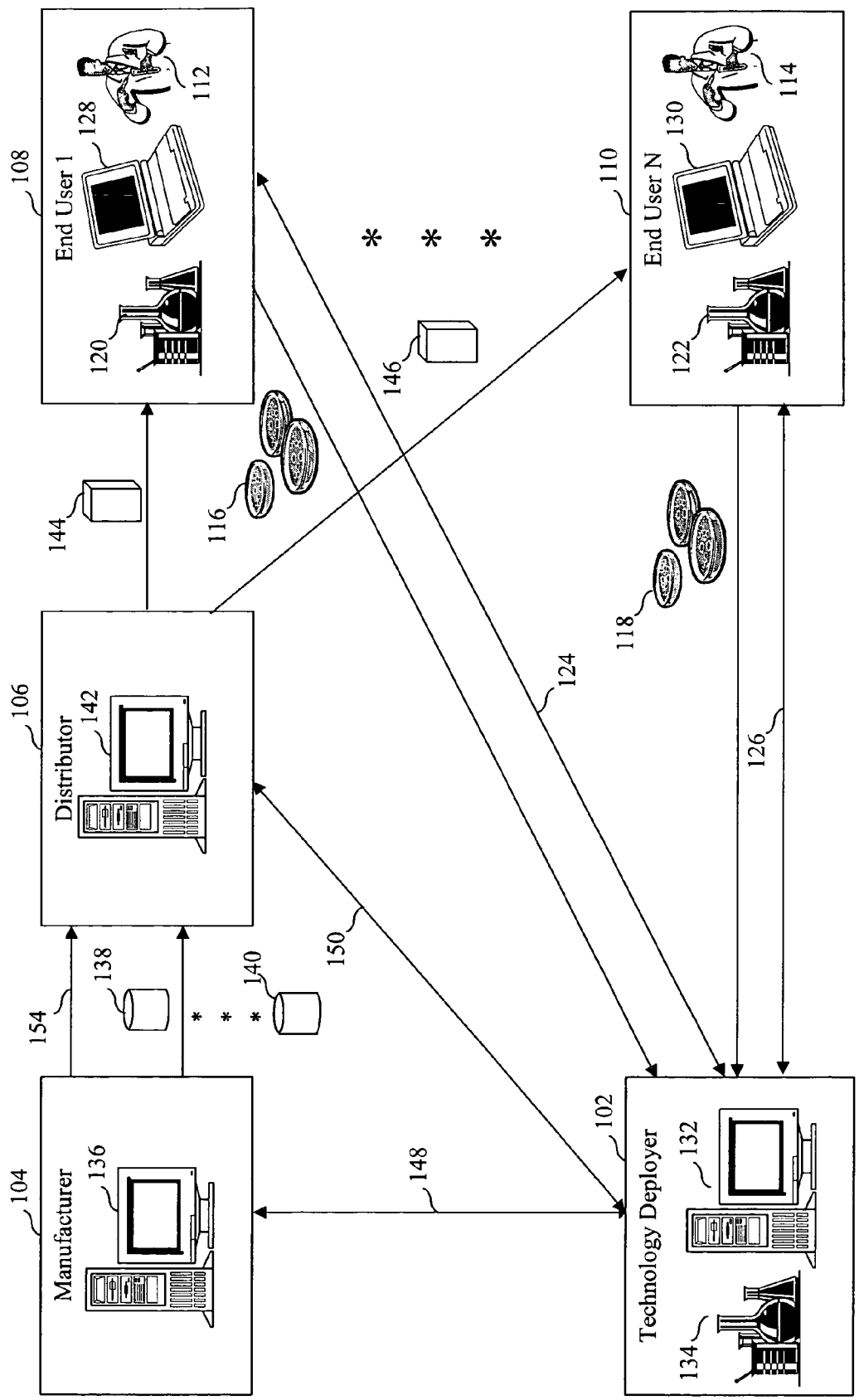
FIG. 1 is a top-level system diagram for control of disease at end user locations, according to the present invention.

The present invention includes recognition that aquatic farmed animals are surrounded by a milieu that supports opportunistic pathogens independently of the host animal, and so the bacterial populations, including pathogens, can reach high abundance around the animal [3]. *Vibrio* grow attached to algae, and may reach high population densities after being ingested with the algae and then excreted with lysed algae in faecal pellets by zooplankton; they are gut bacteria in fish and prawns/shrimp as well as zooplankton [5]. In aquaculture ponds, where animal and algal population densities are very high, *Vibrio* numbers are also high compared to the open sea. Where pathogen numbers are high the phenomenon of quorum sensing can come into play, and result in the activation of virulence genes that would not be turned on when population density is low [27]. The onset of prawn disease due to exposure to high numbers of *Vibrio*, especially when pathogenicity has increased by overuse of antimicrobial compounds, indicates that a defense is needed.

The species composition of a microbial community, such as that in a pond, will be determined partly by stochastic phenomena, that is, chance, and partly by physiological factors. In other words, there are both predictable and unpredictable factors that allow one species to grow and divide more rapidly than others, and thus dominate numerically. Chance favors those organisms that happen to be in the right place at the right time to respond to a sudden increase in nutrients, e.g. from the lysis of algal cells or the decomposition of feed pellets that fall around them. The farmer can manipulate the species composition by seeding large numbers of desirable strains of bacteria or algae; in other words, by giving chance a helping hand [13, 14].

Competitive exclusion is one of the ecological processes that can be manipulated to modify the species composition of a soil or water body or other microbial environment. Small changes in factors that affect growth or mortality rates will lead to changes in species dominance. We are still a long way from knowing all the factors that control bacterial species growth rates and even the complete species composition in natural environments, but enough is known to argue that it is possible to change species composition by making use of competitive exclusion principles [13, 14]. Thus bacteria can compete by secreting antimicrobial compounds that do not necessarily kill all their competitors, but increase mortality rates just enough to tip the balance in resource utilization. For example, if a *Bacillus* strain produces an antibiotic that inhibits a *Vibrio*, then the *Vibrio*'s mortality rate would increase, shifting the dominance to the *Bacillus*, even if the antibiotic were not produced at high enough concentration to kill all or most *Vibrio* cells directly.

Microbial ecology and biotechnologies have advanced in the last decade, to the point that commercial products and technologies are available for treating large areas of water and land to enhance population densities of particular microbial species or biochemical activities. The practice of bioremediation (or bioaugmentation) is applied in many areas, but success varies greatly, depending on the nature of the products used and the technical information available to the end user. The bacteria that are added must be selected for specific functions that are amenable to bioremediation, and be added at a high enough population density, and under the right environmental conditions, to achieve the desired outcomes [13]. Bioaugmentation and the use of probiotics are significant management tools, but their efficacy depends on understanding the nature of competition between particular species or strains of bacteria. They rely on the same concepts that are used successfully for soil bioremediation and probiotic usage in the animal industry.

Probiotics such as the Gram positive *Bacillus* offer an alternative to antibiotic therapy for sustainable aquaculture. *Bacillus* species are commonly found in marine sediments and therefore are naturally ingested by animals such as prawns that feed in or on the sediment. There are several reasons why it is better to add *Bacillus* rather than antibiotics to control *Vibrio* species. Many different antibiotic compounds are naturally produced by a range of *Bacillus* species. Other bacteria are unlikely to have resistance genes to all the antibiotics at one time, especially if they have not been exposed to the *Bacillus* previously. *Bacillus* secrete many enzymes that degrade slime and biofilms and allow *Bacillus* and their antibiotics to penetrate slime layers around Gram negative bacteria. Furthermore, *Bacillus* compete for nutrients and thus inhibit other bacteria from growing rapidly. Thus any resistant bacteria cannot multiply readily and transfer resistance genes. *Bacillus* also compete for space on surfaces (e.g., the gut wall, etc.) and displace other bacteria and prevent their population density from becoming too high [12-15].

The composition of microbial communities in aquaculture ponds and tanks can be changed by adding selected probiotic bacteria that displace and directly inhibit deleterious bacteria and virus under appropriate physico-chemical and biological conditions, thus affording biocontrol of diseases. Mortalities of shrimp and fish caused by pathogenic luminous *Vibrio* species bacteria and virus can be controlled in this manner [12, 15]. The addition of beneficial microbes to aquaculture systems can also improve water quality by speeding up processes of waste degradation, nitrification and denitrification [8, 9]. Control of disease in shrimp and fish culture can be achieved by mixing selected microbial species directly into the water and into the feed of the animals.

Furthermore, manipulating physico-chemical factors can alter the microbial community composition of water bodies, which is influenced by the physico-chemical environment. Thus disease control is an integration of adding selected microbes to animal containment systems such as ponds and to the feed, and adding various chemical compounds and changing physical factors, such as water mixing rates.

Accordingly, microbial biotechnology can provide a solution to the most serious problems in aquaculture and can be applied to every link of the aquaculture value chain: from use of direct-fed microbials in aquafeeds for all life cycle stages (e.g., broodstock, larvae, juveniles, adults. etc.), to bio-augmentation of hatchery, nursery, grow-out and transport water systems, and more.

It is important to recognize that management of microbial ecology through the application of biotechnology to aquaculture is not simply a cure after the disease occurs, but a preventative process and that virus diseases are not easy to control. Positive results can be achieved when attention is paid to all facets of pond and hatchery operations. Thus, according to the present invention, successful management of White Spot Virus and other diseases requires establishment of best practices and training services to manage pond ecosystems, with particular emphasis on the microbial community.

The use of probiotics in fish culture is less developed than in shrimp culture, but probiotics that control fungus (e.g., Saprolegnia) and bacterial gut disease (e.g., *Aeromonas*) in a high value fish (*Lates calcarifer*) have been found. Accordingly, the present invention extends into the fields of fish culture and other aquatic animals.

Thus, with the present invention, a great opportunity to capture market leadership in biocontrol of disease through the application of microbial biotechnology to manipulate microbial communities in the gut and water and to create customer-specific solutions to disease is possible. The present invention will allow this result to be achieved by: (i) applying expert understanding of the physical, chemical and biological factors that affect disease control in commercial aquaculture systems, (ii) providing technical support at the end user location and training aquatic farmers to manage the microbial ecology of the pond and of the gut of aquatic livestock through use of appropriate biotechnology, (iii) directing and using technical information generated by end user to deploy appropriate technological responses to prevent and manage epizootic conditions (iv) providing products containing inhibitors of quorum sensing molecules in bacteria and/or microbial products specifically designed to prevent disease in commercial aquaculture systems, (v) providing products containing inhibitors of quorum sensing molecules in bacteria and/or highly concentrated microbial products that are affordable by end users, (vi) providing products containing inhibitors of quorum sensing molecules in bacteria and/or microbial products that are very user-friendly and (vii) integrating one or more of the items (i) to (vi) described above with the economic and production objectives of animal producers allowing effective biocontrol of disease where none exists today.

The deployment of the technology of the present invention is preceded by an evaluation of the production economics factors of the end user, for example, including livestock survival rate, growth rate, feed conversion ratio, biomass yield, costs of seedstock, costs of feed, costs of fertilizer and other additives, costs of energy, costs of labor, costs of overhead and associated break-even financial points as affected by the market price of livestock produced. The evaluation of the production economics factors described above results in an economic production model that is used to predict the value created by the technology solution of the present invention taking into account the financial investment by the end user in the technology products of the present invention. The model predicts the effects on revenue and overall profitability of the end-user on a per-crop and crop-to-crop basis and helps to establish the economic framework on which the technology solution is created for individual end users.

Referring now to the drawings, wherein like reference numerals designate identical or corresponding parts throughout the several views and more particularly to FIG. 1 thereof, there is shown an embodiment of the present invention.

The system of FIG. 1 includes a technology deployer 102, a manufacturer 104, a distributor 106, end users 108 to 110 and field technicians/end user advisors 112 to 114. It is noted that when those performing the function of 112 to 114, are the technical staff that work under contract, or are employees or agents of the technology deployer 102 and/or distributor 106, they can be referred to as Technology Deployment Managers (TDMs). However, the function of 112 to 114 can be performed by field technicians that are employees or agents of the end user 108 to 110 and that have been appropriately trained by the technology deployer 102. In FIG. 1, microbial samples 116 to 118 (e.g., pathogenic *Vibrio*) are collected by the field technicians 112 to 114 at the end user locations 108 to 110. Physico-chemical data (e.g., dissolved oxygen concentration, Ca concentration, pH, $CO_2$ concentration, salinity, etc.) are determined/analyzed (120 to 122) and transmitted (126 to 124) from field computers 128 to 130 to the technology deployer 102 computer 132. The determinations and analyses of the physico-chemical data from end user 108 to 110 locations are used to generate technical recommendations for the end user 108 to 110 and these technical recommendations are transmitted back (126 to 124) to the end user 108 to 110. These technical recommendations with regard to physical-chemical data can also be generated on site by the end user advisors 112 to 114. A laboratory and computer 132 of the technology deployer 102 analyzes (134) the microbial samples 116 to 118 to determine microbial strain composition and/or quorum sensing molecule inhibitor identity to formulate products and strategies to control and/or manage disease at the respective end user locations 108 to 110 and transmits (148) the product design parameter and/or composition formulations to a computer 136 of the manufacturer 104. The determination of product design parameter and/or composition formulations include, for example, molecular and/or biological analyses of samples 116 to 118 to identify probiotic microbial bacterial strain(s) that can be used to help manage the disease-causing biological samples 116 to 118 by producing enzymes, antimicrobial compounds, antibiotics, quorum sensing inhibitors and quorum sensing molecule enzyme degradation mechanisms that inhibit the growth and/or pathogenicity and thereby help manage disease related to the samples 116 to 118 (e.g., as described in PCT Application Serial Number PCT/US/16489 filed on 22 Jun. 2001). The manufacturer(s) 104 then manufactures the products consisting of microbial strain compositions and/or quorum sensing inhibitor compounds 138 to 140 in concentrated form that then are sent to the distributor 106. A computer 142 at the distributor 106 may also receive information 150 from the computer 132 or information 154 from the computer 136 for further processing and/or custom blending of the microbial strain compositions and/or quorum sensing inhibitor compounds 138 to 140 (e.g., carrier formulae, processing parameters, chemicals for spore activation, enrichment or supplementation with specific microbial strains or chemicals in distributors inventory etc.), before being distributed as end user 108 to 110 specific products 144 to 146. Thus, the distributor 106 may have appropriate ingredients already in inventory to custom blend products and/or further process products per information 150 provided from the computer 132 or per information 154 provided from computer 136.

The present invention thus includes training the distributors 106 and the end users 108 to 110 to manage the microbial communities of aquatic farms with the aid of the microbial biotechnology products including probiotics and/or quorum sensing inhibitor compound products 144 to 146 and technical training services provided by the field technicians 112 to 114 at the end user locations 108 to 110. The application of bio-control technology according to the present invention allows end users 108 to 110, such as aquatic farmers, etc., to eliminate the use of inappropriate or deleterious chemicals and antibiotics, which are harmful and largely ineffective. Once trained in the process of bio-control of disease with technology according to the present invention, distributors 106 can expand their business replacing use of harmful drugs and chemicals. The term bio-control as used herein refers to the use of beneficial, naturally occurring microorganisms and quorum sensing inhibitor compounds to prevent the infection and spread of disease in aquatic livestock.

According to the present invention, microbial technology products include probiotics and/or quorum sensing inhibitor compounds 144 to 146, such as organic supplements and organic concentrates for aquaculture, and typically are sold in the form of dry powders and granules and are also available in liquid form. These products are exported to the distributors 106, who dilute and blend them according to information/ guidelines 150 and/or 154 for forming fertilizers, feeds and other products enhanced with microbial technology as the principal active ingredient. Fertilizers and feeds containing or carrying microbial technology are applied by the end users 108 to 110, such as a shrimp or fish producer, etc., directly at the end user locations, such as, a pond, tank, etc., where the probiotic component of the microbial technology grow and flourish, fighting pathogenic bacteria and viruses in the water and in the gut of aquatic farm animals, preventing infection and death.

According to the present invention, technical training services to enable the end user to develop and apply bio-control programs fully and achieve harvests and yields that typically are far superior to previous productions are provided via field technicians/advisors 112 to 114. For example, end users 108 to 110, such as shrimp producers, fish producers, etc., that use the products 144 to 146 according to the present invention typically can eliminate the use of harmful chemicals and drugs in their animal production and prevent this route of entry into the human food chain. The products 144 to 146 according to the present invention include safe, environmentally friendly bacterial isolates from nature, broadly classified as probiotics, and also quorum sensing inhibitor compounds that are natural products isolated originally from marine algae [26] and are synthesized commercially. Because the products 144 to 146 according to the present invention typically are not genetically engineered, the products 144 to 146 typically do not have restrictive regulatory requirements. Accordingly, the business potential is excellent with large international markets ranging from Latin America to Asia and where disease is a major threat to aquaculture.

The present invention could help the end users 108 to 110 combat complex disease situations where environmental conditions are extreme and different from those in other shrimp producing regions, for example where the salinity is very high. According to the present invention, individual strains of microbes and/or quorum sensing inhibitor compounds 138 to 140 that provide most protection against specific pathogens 116 to 118 affecting the culture systems of the end user 108 to 110 are selected and new environment-specific products 144 to 146 are developed. In most shrimp producing countries the products 144 to 146 according to the present invention may be sold to all major shrimp farms.

A focus of the present invention includes a strategy where products 144 to 146 are continually developed against specific pathogens 116 to 118 for the end user 108 to 110 working in specific environmental conditions in addition to core products that provide protection broadly throughout the aquaculture industry. For example, if a new pathogenic strain of *Vibrio* were identified in a high salinity region, products 144 to 146 can be developed according to the present invention to fight that strain of *Vibrio* specifically. The microbial technology products 144 to 146, developed according to the present invention, could provide control of disease in a very broad range of environments and under adverse conditions. According to the present invention an intensive R&D program 134 is used to develop products 144 to 146 against new viral and bacterial pathogens.

Figure 2:
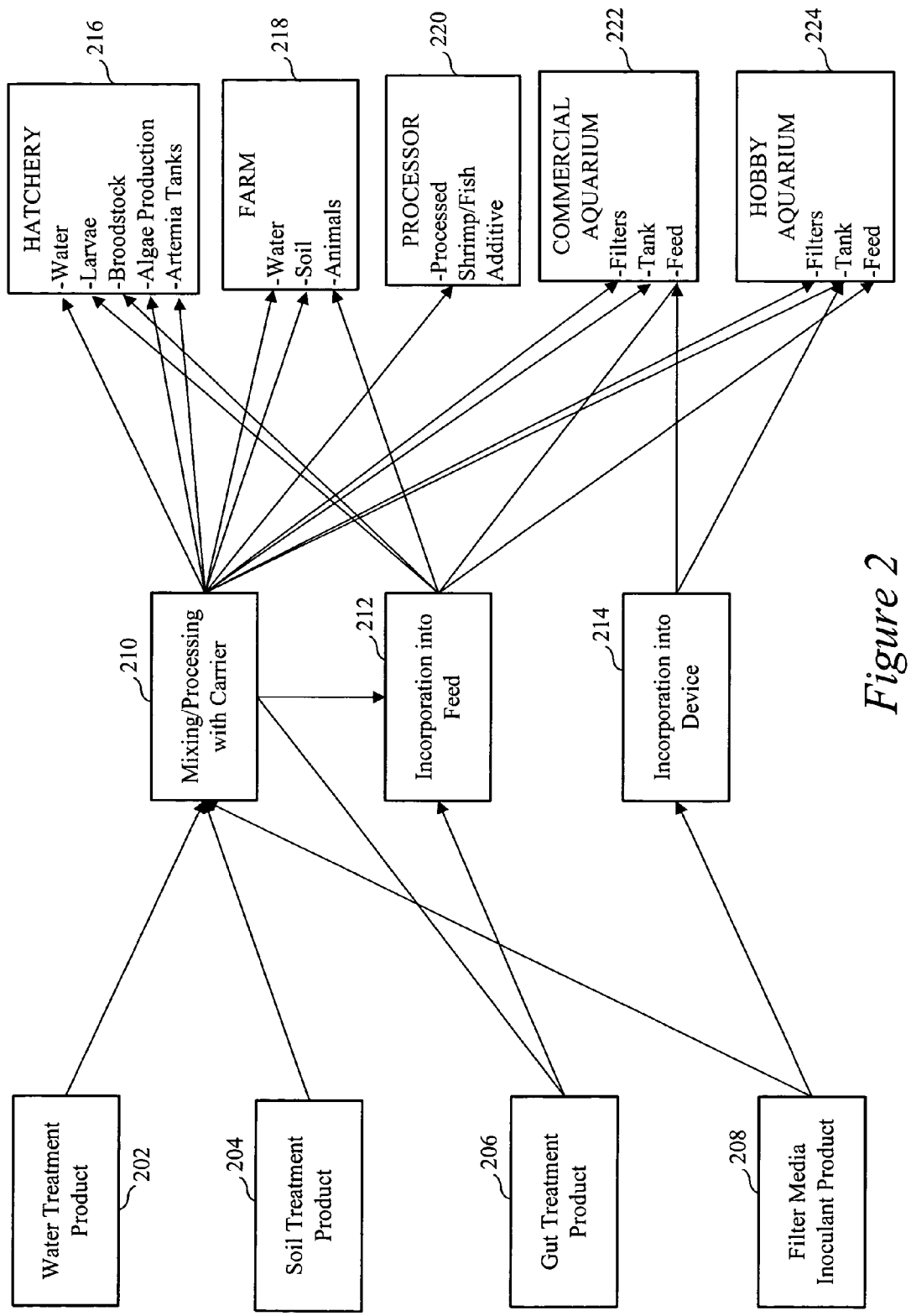
FIG. 2 is a diagram of products, processing and end user applications, according to the present invention.
Figure 3:
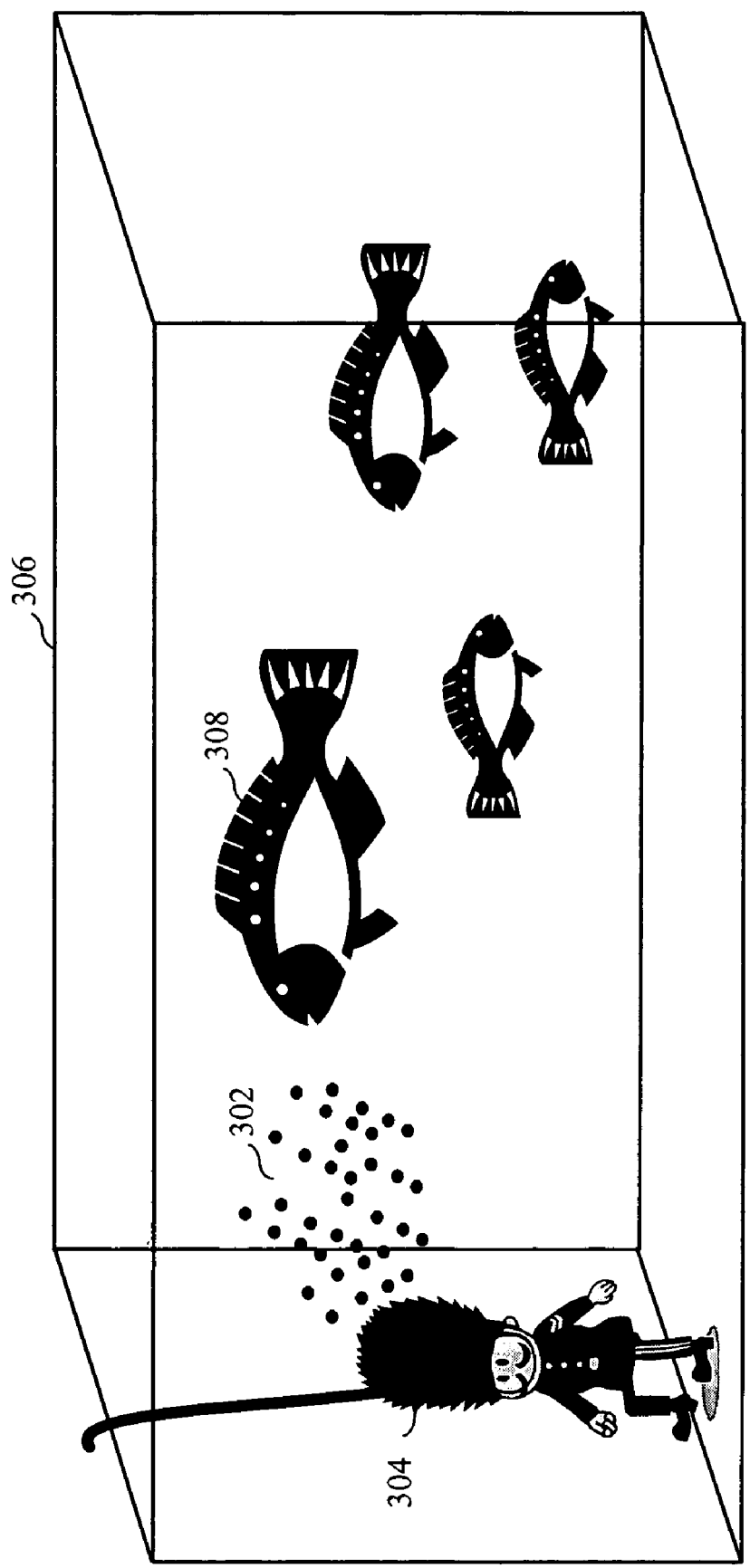
FIG. 3 is a diagram of a product application to a commercial and/or hobby aquarium, according to the present invention.

According to the present invention, Technology Deployment Managers (TDMs) 112 to 114, trained and ready to support the end users 108 to 110 and the distributors 106 are provided, while laboratory scientists, microbiologists and technical assistants (not shown) support product development work. As shown in FIG. 2, microbial technology products 202 to 208 are developed and further processed 210 to 214, field tested and commercialized into new commercial aquaculture end user markets 216 to 220 including, for example, trout and salmon, tilapia, sea bass, sea bream, snapper, eel, crab, turtle, scallops, oysters, pearl oysters, abalone, sea urchin, etc., are possible according to the present invention. The present invention further includes application of products for disease control and water quality into the home and commercial aquaria end user markets 222 and 224 including, for example, pet stores, fish and crustacean transport and holding facilities, restaurants, and high-density, closed fish production systems, etc. This application further includes microbes for bio-filters in such systems. FIG. 3 illustrates an exemplary device 304 in the form of a collectable character for delivering microbes 302 in an aquarium 306 to help manage the microbial ecology of the aquarium 306 and thus prevent disease in fish 308.

Figure 10:
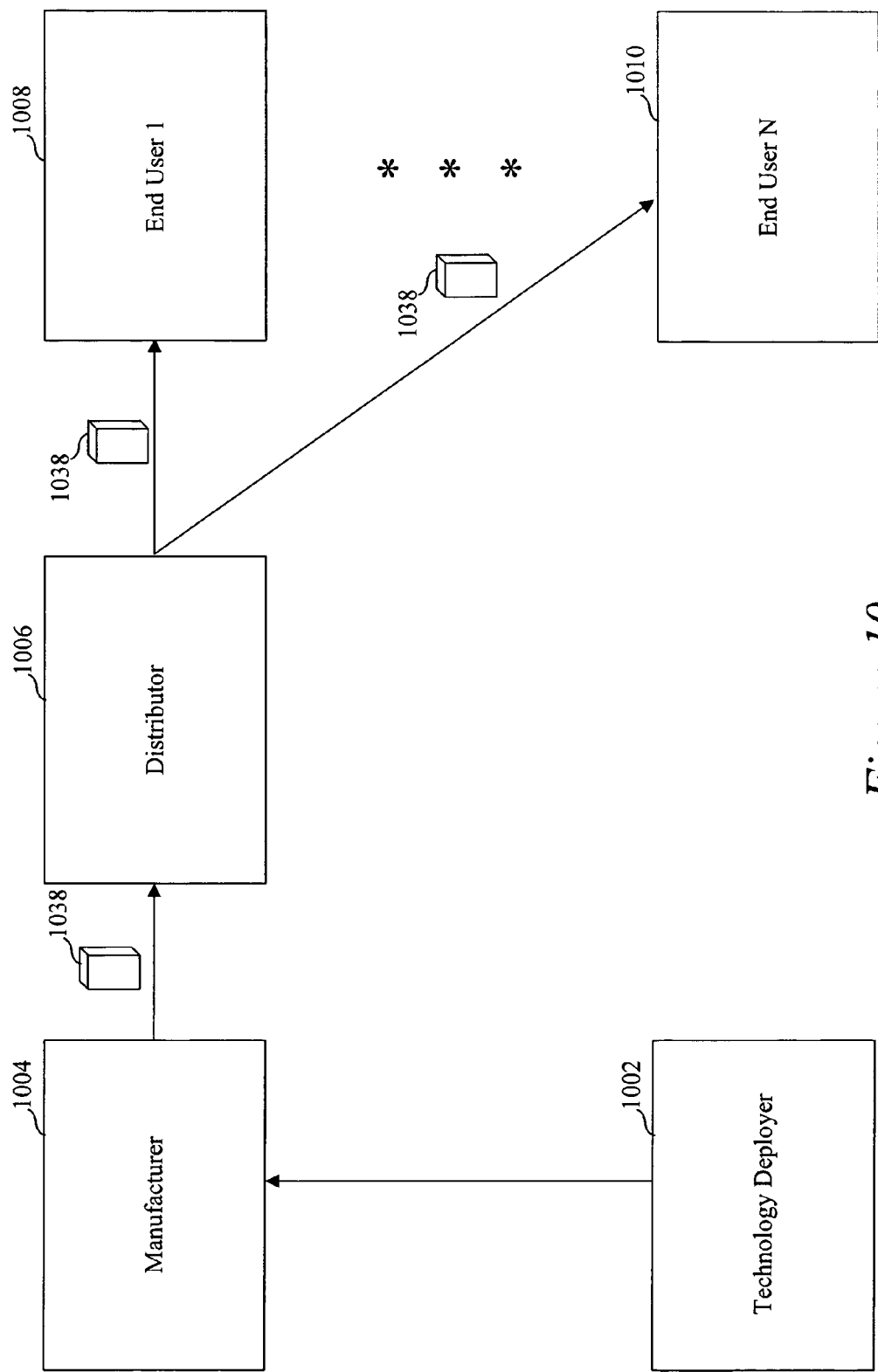
FIG. 10 is a top-level Background Art system diagram.

A business strategy according to the present invention is to combine the market and technical strengths of the technology deployer 102 and with least-cost production strengths of the manufacturers 104 to form a unique synergy, because of the facts that: (i) the manufacturers 104 excel and focus in manufacturing bacteria or quorum sensing inhibitor compounds, which are highly specialized processes, (ii) a manufacturer 104 typically has strong capability in development of bacterial products sold to final product manufacturers 106 and (iii) the technology deployer 102 has market and technical strengths not possessed by the manufacturer; and (iv) some manufacturers 104 typically have strong capability in complex organic chemical synthesis. Thus, by combining the strengths in manufacturing with applied the R&D, expert understanding and experience of the aquaculture market, technical innovation and sales and marketing strengths, such a combination has a strong advantage over competitors (e.g., example as described with respect to FIG. 10) that are typically weak in manufacturing of bacteria and do not understand aquaculture markets or microbial ecology of aquaculture systems.

However, this is not to say that all critical functions ranging from R&D to manufacturing to technology deployment to sales and marketing can not be present in a single business entity that contains in all of these skills, talents and functionalities among the operational units of a single business entity formed for such a purpose.

Figure 4:
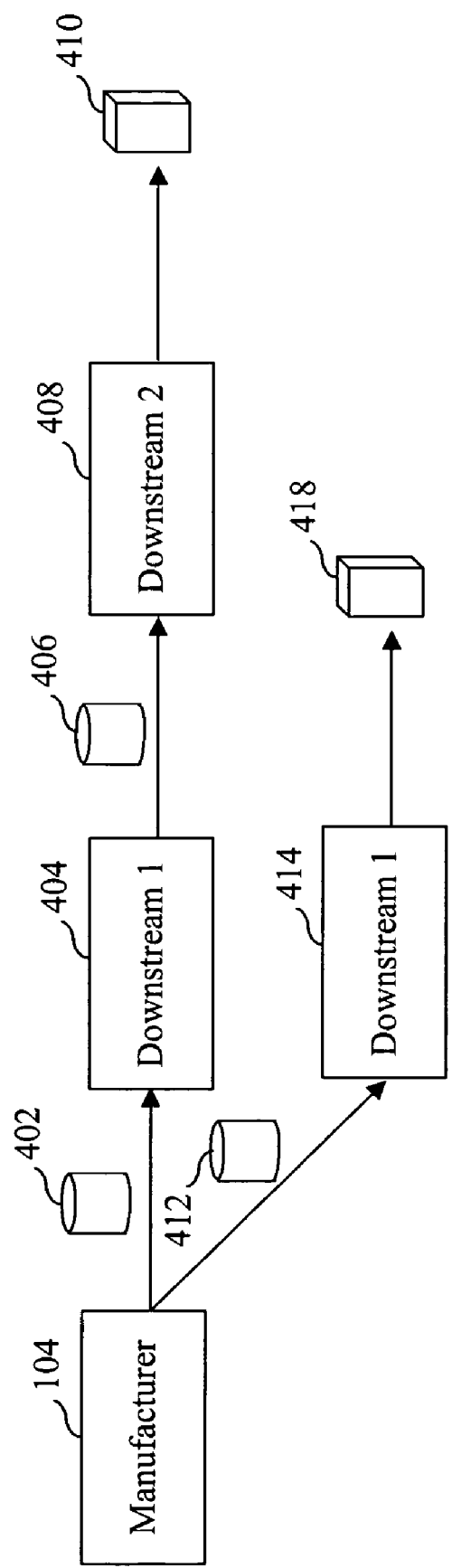
FIG. 4 is another embodiment of the system of FIG. 1 further including one or more downstream manufacturers, according to the present invention.

According to FIG. 4, the business strategy according to an embodiment of the present invention takes advantage of least-cost manufacturing 104 of highly concentrated products 402, 412 that, for example, are: (i) further processed by a downstream manufacturer (404) into organic supplements (406) for aquaculture and shipped to international distributors (408) who further dilute or process the products into feeds (410) for animals or (ii) shipped directly to international distributors (414) as organic concentrates (412) for aquaculture and then are further processed (418) in-country. These strategies according to the present invention keep freight costs low by shipping low volumes of concentrated products (402, 412) directly into aquaculture markets and help keep aquaculture production costs low while managing disease.

According to the present invention, core market entry products are sold under an umbrella trade mark and are comprised of two types: (i) those added to aquaculture pond water (referred to as "aqua" products) and (ii) those added to the feed of aquatic animals (referred to as "feed" products). All products typically contain as an active ingredient, a blend of one or more species and strains of naturally occurring, benevolent microbes in a dry powder form and/or quorum sensing inhibitor compounds. Products are also available in liquid form, as needed, for appropriate applications.

According to the present invention, there are, for example, two export categories: (i) organic supplements and (ii) organic concentrates. The organic supplements and organic concentrates can be standardized to a net weight with animal feed ingredients during further processing. The above-noted products are summarized in Table 1 below.

TABLE 1

Microbial Technology Products for Export

Aqua Product 1—An organic supplement for aquaculture (aqua) including microbes and/or quorum sensing inhibitor compounds blended with animal feed quality byproducts, steam pelleted, crumbled and packaged into 5 to 50 kg Net Wt containers such as plastic bags in cardboard boxes.
Aqua Product 2—An organic concentrate for aquaculture (aqua) including microbes, fermentation byproducts and single-cell protein products in dry powder or liquid form and/or quorum sensing inhibitor compounds and packaged in plastic-lined barrels, buckets or drums.
Feed Product 1—An organic supplement for aquaculture (feed) including microbes and/or quorum sensing inhibitor compounds blended with animal feed quality by-products, steam pelleted, crumbled and packaged into 5 to 50 kg Net Wt containers such as plastic bags contained in cardboard boxes.
Feed Product 2—An organic concentrate for aquaculture (feed) including microbes, fermentation byproducts and single-cell protein products in dry powder or liquid form and/or quorum sensing inhibitor compounds and packaged in plastic-lined barrels, buckets or drums.

Another product according to the present invention is designed for the shrimp hatchery market and is described in Table 2 below. This product is used by end user consumers at low concentrations, added to tank water and is high margin low-volume business. The export form is also the end-used form.

TABLE 2

Hatchery Products

Hatchery Product—organic supplement for aquaculture (hatchery) including microbes, fermentation byproducts and single-cell protein products in dry powder or liquid form and/or quorum sensing inhibitor compounds, packaged in 100 gram to 50 kg containers.

The core aqua products for shrimp farms are further processed by blending with organic materials in country to form value-added microbial and/or quorum sensing inhibitor compound supplements carried as organic fertilizer products. Two concentrations, thus two local products as shown in Table 3 below, are sold locally depending on the method of shrimp farming. The feed product is incorporated directly into the feed of aquatic animals by local feed manufacturers and thus requires no special handing by shrimp farmers.

TABLE 3

Microbial Technology Products for Local Distribution

Local Product 1—Hi Concentration Aqua Product, an organic concentrate or supplement for adding to aquaculture water (aqua) diluted at less than or equal to about 1:1 to 1:5 with formulated carrier ingredients that function as organic fertilizer for shrimp ponds.
Local Product 2—Low Concentration Aqua Product, an organic concentrate or supplement for adding to aquaculture water (aqua) diluted at greater than or equal to about 1:6 to 1:20 with formulated carrier ingredients that function as organic fertilizer for shrimp ponds.

TABLE 3-continued

Microbial Technology Products for Local Distribution

Local Product 3—Feed, an organic concentrate or supplement for aquaculture (feed) added to shrimp feed in the range of about 0.1 to 100 kg per metric ton.
Local Product 4—Hatchery, microbes, fermentation byproducts and single-cell protein products in dry powder or liquid form and/or quorum sensing inhibitor compounds, packaged in 100 gram to 5 kg containers.

According to the present invention, the amount of product typically required by semi-intensive shrimp farmers is 0.1 to 100 kg per hectare per crop.

Training of the distributors 106 and end user 108 to 110 personnel is a feature of the present invention. Farmers need guidance and advice to manage the microbial environment. Therefore, training services in the form of written technical bulletins, guidelines, and interactive multi-media training modules such as through CD ROM or via the Internet, and with hands-on training in customer labs and in the field are provided. The complete training program is focused on adult learning principles.

The immediate customers of the technology deployer 102 are the distributors 106 of feed, chemicals and other products to the end users 108 to 110, such as shrimp farmers, etc. The final end user customers are the aquaculture producers such as shrimp farmers 108 to 110.

Part of the uniqueness of the technology deployer 102, is that it is not simply a production and sales company, but is at the forefront of its scientific fields of microbial ecology and nutrition and brings new products based on new developments in microbial technology to the marketplace for the benefit of its customers.

Typically, all products containing microbes and/or quorum sensing inhibitor compounds are manufactured by the manufacturer 104 and mixed as dried powders or liquids in ratios appropriate to each final product (e.g., pond, feed, hatchery water, hatchery feed, etc., as previously described). The microbial and/or quorum sensing inhibitor products then are shipped to the distributor 106 for further processing, final blending, packaging and/or formulation as feed products. They are mixed with feed materials supplied by other suppliers, and/or fortified or enriched with specific active ingredients, such as microbial strains and/or quorum sensing inhibitor compounds, etc., and then packaged, labeled and shipped to final end user 108 to 110 destination or to another location, depending on customer requirements. In each destination country, distributors 106 or end user farmers 108 to 110 arrange for a feed manufacturer to incorporate the concentrate 144 into a custom feed blend, containing about 0.1 to 100 kg concentrate/tonne feed. Alternatively, end user customers 108 to 110 can buy a final feed mix 144 directly from the distributor 106.

The concentrated forms of the pond products may be formulated as crumble feeds by the distributors 106. The concentrates for feed products (e.g., for blending into shrimp feed) may be formulated as crumble feeds by the distributors 106. The hatchery product concentrates (e.g., for hatchery tank water) may be formulated as powdered or liquid products by the manufacturer 104, then as a feed by the distributors 106.

The business of the technology deployer 102 typically is primarily centered on applications of microbial and/or quorum sensing inhibitor compounds technology, using products that are manufactured under contract. Hence production typically is not a major facet of the technology deployer 102. The production of the microbial and/or quorum sensing inhibitor compound products 138 to 140 is of course complicated, which is why the technology deployer 102 contracts out the process to manufacturers 104 with appropriate skills and facilities. However, all facets of the applications of microbial and/or quorum sensing inhibitor compounds technology and the production of the microbial and/or quorum sensing inhibitor compound products 138 to 140 may be performed by a single business entity formed for such a purpose.

The microbial technology according to the present invention typically is a combination of products and know-how in applied microbial ecology, with the microbes occurring naturally in nature and without further genetic engineering. However, genetic engineering could be used in conjunction with the present invention, as will be appreciated by those skilled in the relevant art(s).

According to the present invention, techniques for controlling *Vibrio* disease using bioactive compounds to turn off genes for virulence (e.g., as described in PCT Application Serial Number PCT/US/16489 filed on 22 Jun. 2001) are also employed. Routine R&D is performed for improving extant products and to select new microbial strains against *Vibrio* and virus pathogens of shrimp.

According to the present invention, data are obtained for local conditions in each country as well as each region, as farmers are (justifiably) conservative and reluctant to accept studies done in other regions before purchasing products. Using the methods described below, the research workers at the laboratory screen a range of potential probiotic bacterial species against pathogenic *Vibrio* strains isolated from farms in each region and select probiotic strains that inhibit the *Vibrio* species, using salt concentrations that are appropriate for the region. For example, in some areas salinity may be as high as 6%, and thus probiotics must be selected that grow at 6% and are active against *Vibrio* or other pathogenic bacteria at 6% salinity.

New hatchery feeds and feed delivery methods that combine probiotic microbes and bioactive compounds (e.g., as described in PCT Application Serial Number PCT/US/16489 filed on 22 Jun. 2001) are part of the present invention, because feeds serve as important vehicles for disease control in the production of shrimp, fish, molluscs and other aquatic animals in hatcheries, which are severely limited by such diseases.

Figure 5:
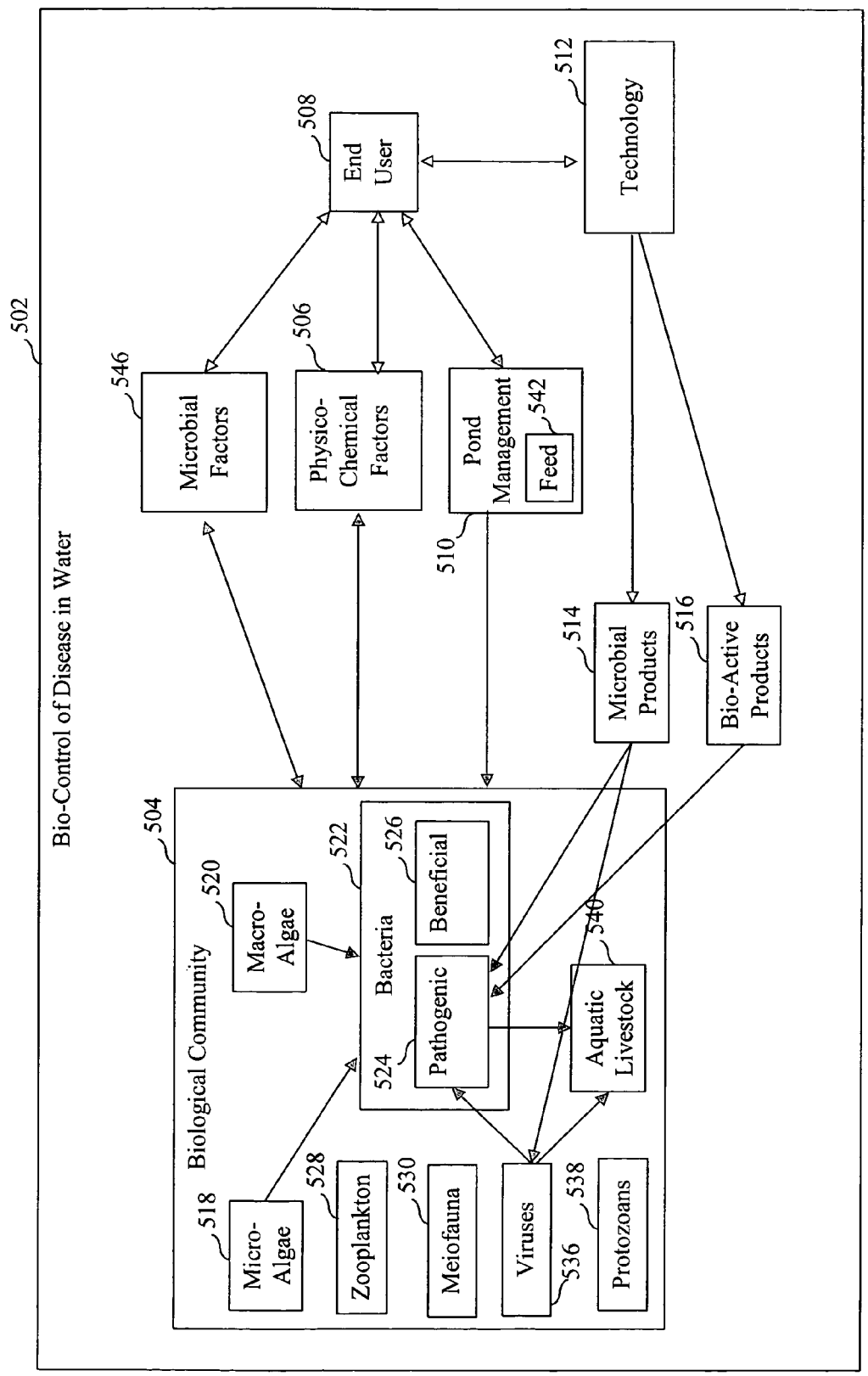
FIG. 5 is a diagram for illustrating bio-control of disease in water, according to the present invention.

According to the present invention, products for disease control are applicable in many industries, not just aquaculture, and involve molecular biotechnology, including bioactive compounds that turn off genes for disease virulence in pathogens (e.g., as described in PCT Application Serial Number PCT/US/16489 filed on 22 Jun. 2001). FIG. 5 is a diagram for illustrating bio-control of disease in water, according to the present invention. In FIG. 5, bio-control of disease in water 502 includes a comprehensive approach of monitoring/managing disease in the biological community 504 using technology 512 to introduce microbial products 514 and/or bio-active compounds (e.g., quorum sensing inhibitor compounds) 516 and to provide technical recommendations (124 to 126 of FIG. 1) for managing the biological community 504, which includes, for example, micro and macro algae 518 and 520, bacteria 522, which includes pathogenic and beneficial bacteria 524 and 526, zooplankton 528, meiofauna 530, viruses 536, protozoans 538 and aquatic livestock 540. The bio-control of disease further includes controlling/collecting microbial factors 546 (116 to 118 of FIG. 1) and physico-chemical factors 506 and performing pond management 510, including providing feed 542, via the technology 512 and the end user 508, as will be further described in detail. Important cause and effect relationships are indicated in the drawing by arrows. The line drawn from viruses 536 to pathogenic bacteria 524 represents control of pathogenic bacteria via inclusion of bacterial viruses as bioactive components according to the present invention.

Figure 6:
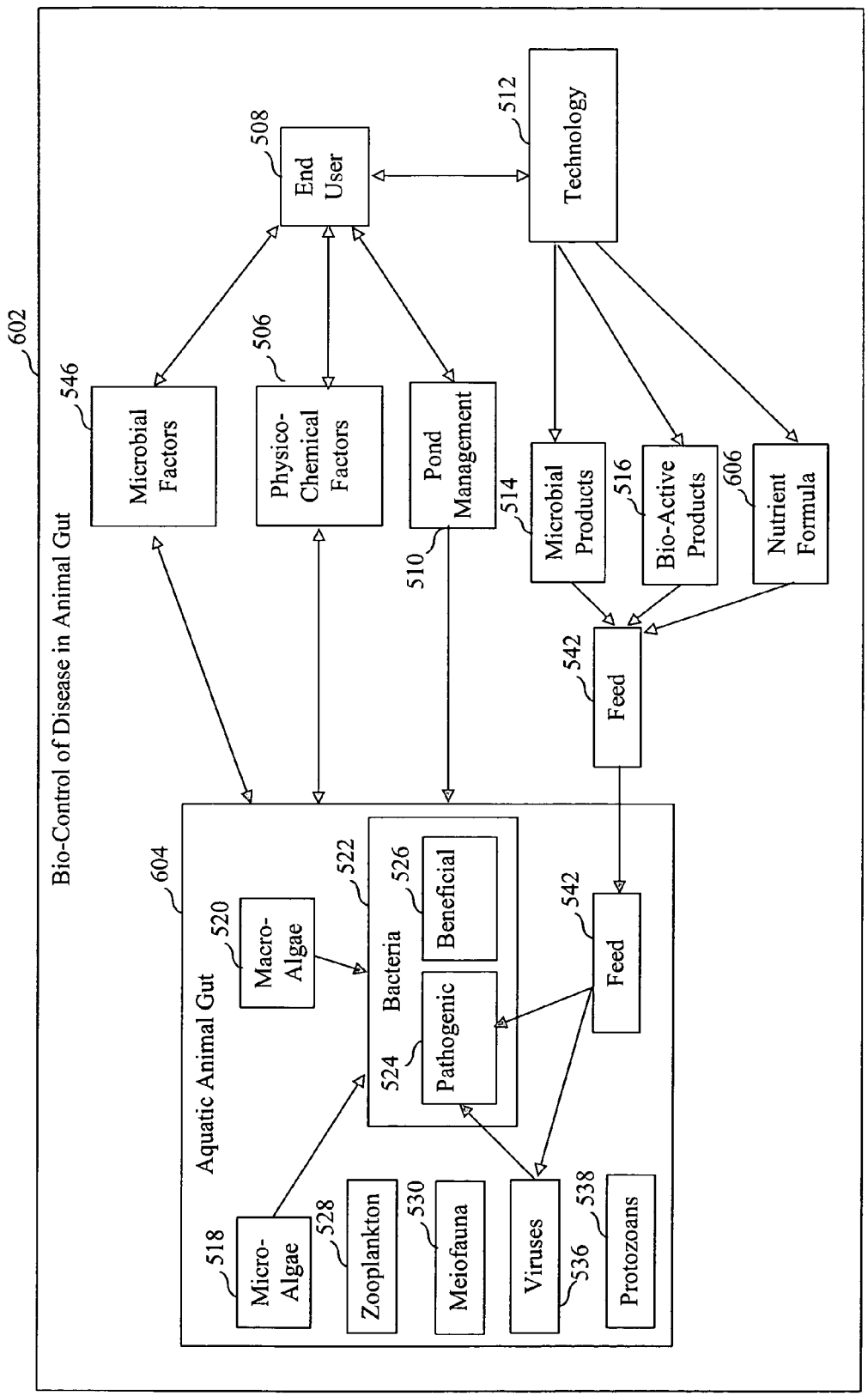
FIG. 6 is a diagram for illustrating bio-control of disease in a gut of an animal, according to the present invention.

FIG. 6 is a diagram for illustrating bio-control of disease in a gut of an animal, according to the present invention. In FIG. 6, bio-control of disease 602 in a gut of an aquatic animal 604 includes a comprehensive approach of monitoring/managing disease in the gut of the aquatic animal 604 using technology 512 introduced via the feed 542 including microbial products 514 and/or bio-active compounds (e.g., quorum sensing inhibitor compounds) 516 and a nutrient formula 606 into the gut of the aquatic animal 604, which can contain as a result of the animal's natural foraging activity, for example, micro and macro algae 518 and 520, bacteria 522, which includes pathogenic and beneficial bacteria 524 and 526, zooplankton 528, meiofauna 530, viruses 536, protozoans 538 and feed 542. The bio-control of disease further includes controlling/collecting microbial factors 546 (116 to 118 of FIG. 1) and physico-chemical factors 506 and performing pond management 510, via the technology 512 and the end user 508, as will be further described in detail. Various cause and effect relationships are indicated in the drawing by arrows.

Figure 7:
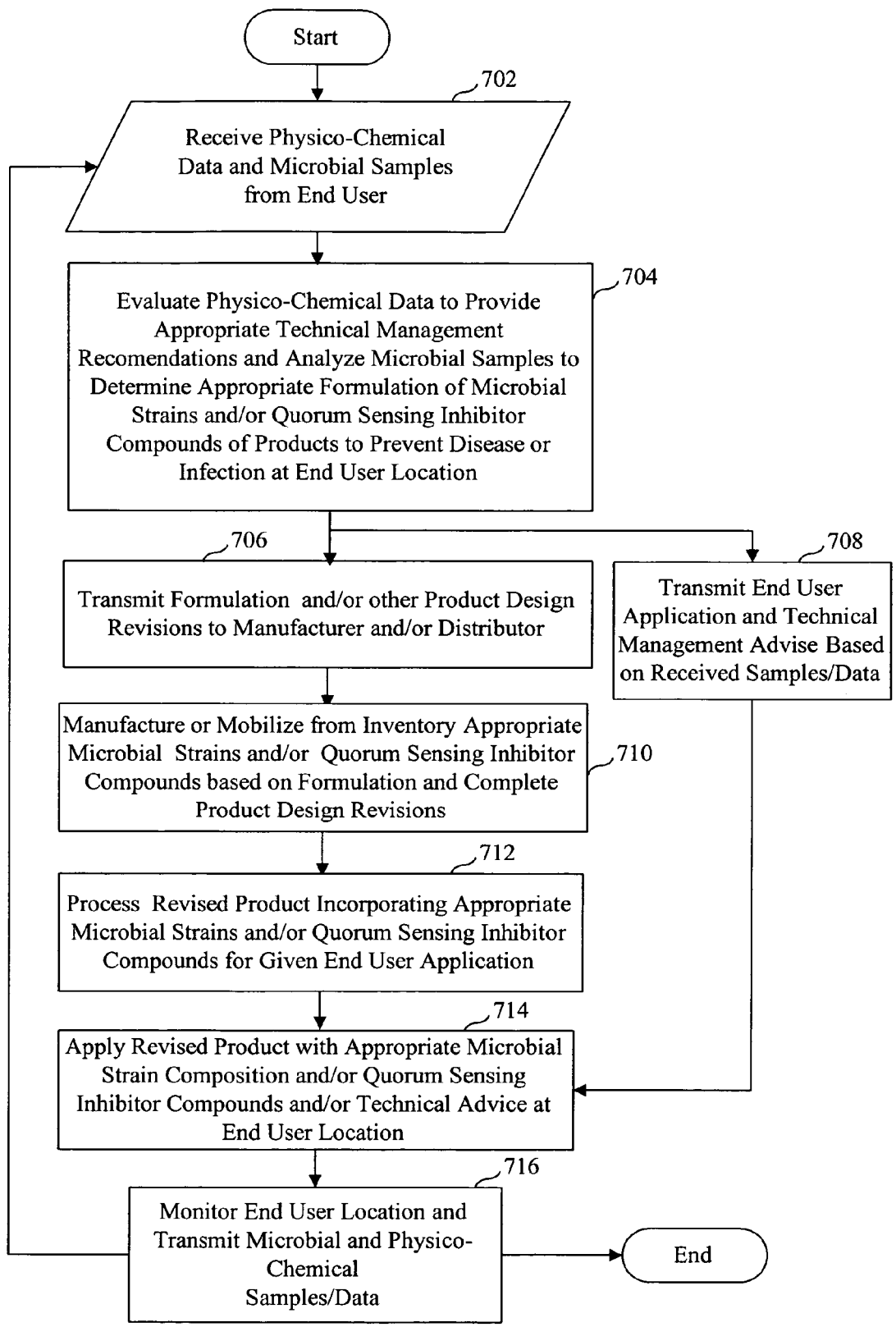
FIG. 7 is a flow chart for illustrating the operation of the system of FIG. 1, according to the present invention.

FIG. 7 is a flow chart for illustrating the operation of the system of FIG. 1 in controlling disease according to FIGS. 5 and 6, according to the present invention. In FIG. 7, at step 702 the microbial samples 116 to 118 are received from field technicians/TDMs 112 to 114 or directly from other end user 108 to 110 staff and the physico-chemical data 124 to 126 are received from the field computers 128 to 130 by the technology deployer computer 132. At step 704, the product design including the microbial strain composition and/or quorum sensing inhibitor compound formulation is determined/modified based on analyses of the received samples 116 to 118 and/or data 124 to 126 and a database of microbial strains and other product design parameters including feed nutrient and feed nutrient formula 606, at the technology deployer computer 132 and/or manufacturer computer 136 and/or distributor computer 142. The formulation may be transmitted by the technology deployer computer 132 to the manufacturer computer 136 and/or distributor computer 142 depending on the level of complexity or simplicity of the product design modifications required to meet the end user 108 to 110 requirements per analysis of samples 116 to 118 and/or data 124 to 126 and a database of microbial strains and other product design parameters. For example, for a relatively simple modification to an existing product design, such a simple fortification or enrichment rather than a complete product re-design, the technology deployer 102 may transmit this information via the computer 132 or by other means of communication to the manufacturer 104 or distributor 106 or directly to computers 136 and 142, respectively. In addition, at step 708, the technology deployer computer 132 may transmit to the end user 108 to 110 end-user-specific technical management advise based on the received samples 116 to 118 and/or data 124 to 126. Such data 124 to 126, formulation, pond management advice, etc., may also be transmitted via any other suitable means, such as by facsimile, wireless communications, telephony, Internet, Intranet, modem, cellular phone, satellite communications, etc., as will be appreciated by those of ordinary skill in the relevant art(s).

At step 710, the manufacturer 104 manufactures the products 138 to 140 based on the formulation. In addition, at step 710, the manufacturer 104 or distributor 106 can mobilize from existing inventory the appropriate microbial strains or bioactive compound or other product components for a revised product design determined at step 704 and transmitted at step 706 to meet revised product design criteria. The distributor 106 may then further process the products for a given end user 108 to 110 application at step 712. At step 714, the respective products 144 to 146 are applied at the respective end user locations 108 to 110. The end users 108 to 110 then monitor the respective end user locations. At step 716, the respective end users 108 to 110 transmit updated microbial and/or physico-chemical samples 116 to 118 and data 124 to 126 to the technology deployer 102, completing the process.

The following sections describe the physico-chemical samples 116 to 118 and data 124 to 126, which are collected and technical advice provided, which is followed by end user to obtain disease control, as described with respect to FIGS. 1-7. The examples below are described for shrimp aquaculture; for culture of other organisms, e.g. tilapia or salmon a different set of data would be obtained and analyzed and instructions provided for the end user. The examples provided above of biocontrol of disease in aquatic organisms takes into consideration the complexity of raising animals in an aquatic environment but can be simplified and adapted for disease control in terrestrial farm animals per the present invention. For example, in the case of swine, poultry or cattle production the physico-chemical factors of the air and drinking water are measured and analyzed and the biological factors associated with the microbial flora of the feed and gut are considered.

Below is a list of physico-chemical and biological factors, their methods of analysis and optimum ranges for shrimp ponds (Table 4). All end users are advised to determine this set of factors at the frequency listed in the table. They record the information in a computerized form and transmit it by electronic means to the distributor and/or the technology deployer who monitor progress and provide advice where needed to bring the factors into the optimum range. The end user is advised or trained where necessary with respect to how to manage the ponds to bring each factor into its optimum range. For example, if calcium is low, then the end user will be advised to add lime; if oxygen is low, to add more aerators or exchange water with filtered clean water (e.g., which may be from a recycling reservoir, etc.).

Methods and Equipment

Kits with full instructions are available from several supply companies dealing in water quality determinations. For a large farm or cooperative laboratory, it is beneficial to have a chemistry and microbiology laboratory with more elaborate equipment and trained staff.

Some factors vary diurnally and should be determined at the same time of day for each sampling period.

Determination of *Vibrio* Bacterial Counts with Selective Media (e.g., Note that Selective Microbiological Techniques May be Applied for other Potential Bacterial Pathogens of Interest)

Use TCBS agar plates or dip slides. Dip Slides are plastic strips with TCBS agar in a sterile container. Dip slides can be taken to the ponds and dipped directly into the pond water. Incubate at 30-35° C. for 12 hours, then count total luminous colonies. Prepare sterile dilution tubes: (i) add 9 mL saline solution in 20-30 mL test tubes with loose caps or cotton plugs; sterilize in autoclave and cool; (ii) water: collect samples of pond water in sterile bottles; (iii) sediment: see above section on sample collection; (iv) keep samples cool: 5-10° C. (refrigerator or ice pack) until ready to plate out. (v) homogenize 2 mL samples.

Hepatopancreas *Vibrio* Counts (e.g., Note that Counts May also be Determined for the Foregut and Haemolymph of Shrimp, as Needed)

Dissect the mid gut or hepatopancreas (mid gut gland) of the shrimp with clean scissors. Place the hepatopancreas in a clean dish. Using scissors cut the hepatopancreas up into small fragments, mix with 20-200 mL sterile saline water and homogenize. Plate out on TCBS agar using standard procedures or pour into clean Dip Slide container and dip the slide briefly, then incubate as described above.

Sediment Collection

Collect top 1 cm of sediment in PVC or Perspex tubes. Place sediment in a clean jar. Mix sediment with 50 mL filtered sterile water. Take 2 ml subsample and homogenize then dilute 10-100 times for in filtered, sterile saline water.

TABLE 4

Factors to be determined in shrimp ponds.

| Factors | Method | Frequency | Optimum Value or Range |
|---|---|---|---|
| 1. Transparency | Secchi disk | daily, 12-1 pm | 35-50 cm |
| 2. Oxygen | DO/Temp meter | daily, 5 am, 12-1 pm | >4.0 ppm |
| 3. Salinity | Refractometer | Weekly | 20-35 ppt |
| 4. Temperature | DO/Temp meter | daily, 5 am, 12-1 pm | 28-32° C. |
| 5. Ph | pH meter | daily, 5 am, 12-1 pm | 8.0-8.3 |
| 6. Vibrio in water | TCBS agar | Weekly | <1000-2000 cfu/ml |
| 7. Luminous Vibrio - water | TCBS agar | Weekly | <10 cfu/ml |
| 8. Vibrio - hepatopancreas | TCBS agar | Weekly | <1000/gut |
| 9. Luminous V. hepatopancreas | TCBS agar | Weekly | <10/gut |
| 10. Alkalinity (units of $CaCO_3$) | chemistry kit | Weekly | 120-130 ppm |
| 11. Calcium hardness (as $CaCO_3$) | chemistry kit | Weekly | 250-400 ppm |
| 12. Phosphate (before stocking) | chemistry kit | 1-2 days | <0.8 ppm |
| 13. Phosphate (until week 4) | chemistry kit | Weekly | <0.5 ppm |
| 14. Ammonium (after week 12) | chemistry kit | Weekly | <0.5 ppm |
| 15. Nitrite (after week 12) | chemistry kit | Weekly | <0.1 ppm |
| 16. Vibrio in sediment | TCBS agar | bi-weekly | <2000 cfu/cc |
| 17. Luminous V. sediment | TCBS agar | bi-weekly | <10 /cc |
| 18. Vibrio in haemolymph | TCBS agar | as desired | 0 |
| 19. Algae: cell counts | Microscope | daily during fertilization | >200,000/mL |

Plate out on TCBS agar using standard procedures or pour into clean Dip Slide container and dip the slide briefly, then incubate as described above.

Water Collection

Collect water near bottom in the ponds for analysis. In large ponds that are not mixed, take several samples from around the pond and pool them to give an average sample.

Luminous Bacteria

The principal species that is luminous on TCBS is *Vibrio harveyi*, although not all strains of this species are luminous. There are other luminous strains among other *Vibrio* genera, e.g. *V. fisheri*, *V. cholera* and *V. splendidus*. In general (but there are always exceptions), only luminous *Vibrio* luminesce on TCBS. The end user is advised to adjust dosing of the microbial technology products to keep luminous *Vibrio* numbers low or absent. If this cannot be achieved, then the end user advises the distributor 106 and/or technology deployer 102 who will proceed to determine whether new or revised products are needed or advise on varying application of current products.

The following section describes a summary of the shrimp pond sampling procedures, and the type of advice given to the end users 108 to 110 (e.g., shrimp farmers) to maintain water in optimum condition according to Table 4, so that added microbes can operate at optimum efficiency in controlling pathogenic bacteria and viruses. By responding to advice regarding these parameters, the end users 108 to 110 can maintain water at a high enough quality to reduce the environmental stress on the aquatic livestock and help assure that the microbial products can work effectively. As a consequence of making the physico-chemical determinations, the end users 108 to 110 can be guided by the technology deployer 102 according to the present invention in the most effective technical management strategy.

Aeration to maintain dissolved oxygen concentration above 4 ppm and preferably above 5 ppm, and mixing to maintain organic material in suspension with no deposition of organic sludge on the pond bottom, are important to help assist in maintenance of good water quality, which in turn allows added microbial products to work effectively.

Pond Preparation on Potential Acid Sulphate Soils

New Ponds: flush 4 to 5 times, preferably with fresh (non-saline) water. Between each flushing episode, allow pond to dry out and sediments become exposed to air for 2 to 3 days before flushing again. Monitor pH before and after flushing. When pH changes by less than 1 unit, drain the pond, and apply hydrated lime (calcium hydroxide) at 1 tonne/hectare across the soil. Then, apply agricultural lime (calcium carbonate) or dolomite at 2-5 tonne per hectare. Fill the pond with water and monitor pH. If it is less than pH 8.0, add more calcium carbonate. Between crops, the pond should be dried if possible, and black sludge removed. Monitor soil pH. If it less than pH 8.0, add 200-500 kg hydrated lime/ha and 1-2 tonne/ha calcium carbonate or dolomite; the lower the pH, the larger the dose of lime that should be added.

Products Added to the Aquafarm Pond Water

The hydration procedure for Aqua Product microbial technology is as follows, but quantities and concentrations can be modified as needed: (i) use 1 kg per hectare per application; (ii) for each 1 kg of Aqua product, take 4 liters of fresh water If fresh water is not available, then use seawater that has been chlorinated for 24 hours with 100 ppm chlorine, then acidified, aerated and neutralized; (iii) add the Aqua product powder to a clean bin or other container that can be covered, then mix in the water; (iv) cover the bin and stand for 12 hours, then mix with organic fertilizer or apply to feed; (v) hygiene is very important, wash hands before preparing the Aqua Product suspension and wash all containers and mixing utensils before and after use.

Organic Fertilizer Medium for Aquatic Farm Ponds

The fertilizer medium is prepared as follows: (i) prepare hydrated Aqua product as described above 1 day before use; (ii) for each hectare, prepare a fermentation medium as follows: (a) yeast: 250 g, (b) soybean meal or meal flour: 25 kg, (c) rice bran: 25 kg, (d) fresh water 200 liters, and (e) urea: 5 kg (see above: only if Secchi transparency is <60 cm) and soluble phosphate: 200 g (only if phosphate concentration in pond water is less than 0.1 ppm); (iii) mix together and add the 12 hour hydrated Aqua Product; and (iv) incubate for 2-3 days then spread over the pond (if aeration is available, aerate during the incubation period).

Advice for Disease Control in Ponds With No Aeration.

At low stocking density typical of non-aerated ponds, applying disease control technology can be made more efficient by holding the postlarvae (seedstock) in an encierro, i.e., an enclosure comprised of netting stretched across a pond or forming a cage within the larger pond, or in a nursery pond or raceway for 30 days after stocking or longer if possible. Animals should be concentrated at a high enough stocking density in the encierro enclosure to force them to eat artificial feed containing the microbial technology of the present invention. Before proceeding, farmers are advised and coached through a cost analysis in relation to production objectives and variable such as stocking density, expected survival to determine the maximum encierro size consistent with costs and expected financial returns for a given pond or set of ponds.

Encierros are built to have one or more phases or stages of enclosure for progressively larger animals. For example, start with an encierro of about 500 to 700 square meters or of a size sufficient to hold newly stocked animals at a density of about 1000 to 5000 per tonne of water, then release animals into the second stage of 2500-3000 square meters or of a size sufficient to hold animals at a density of about 250 to 1000 per tonne of water, then release animals into a larger encierro of about 10,000-20,000 square meters pond area or of a size sufficient to hold animals at a density of about 50 to 250 per tonne of water. Release the animals from the smaller to larger encierros progressively, or transfer animals from smaller to larger containment systems (e.g., ponds, tanks) when growth starts to slow down, for example before oxygen concentrations fall below 4 ppm and before the daily feeding rate reaches about 12 kg feed/ha/day. This will help maximize the amount of time the animals are in water that is treated by the microbial technology of the present invention. An encierro can be made by placing a net of fine mesh (e.g., 0.5-1.0 mm) for smaller encierros or other inexpensive barrier material around the water inlet or exit or from dyke-to-dyke across the pond. The second net can be less expensive and made of a larger mesh to hold larger animals. Feed trays should be used at all times. It is best to apply as much feed as practicable to trays. Feed trays may be placed around the edge of the encierro for easy access, or to stakes across the pond or encierro.

The encierros should be treated with Hi Concentration Aqua Product at least 2 days before stocking and then at 3-4 day intervals. In general, for newly stocked animals held at a density of about 1000 to 5000 per tonne of water, apply 1 kg of hydrated Hi Concentration Aqua Product per 1,000 square meters of encierro surface; for animals held at a density of about 250 to 1000 per tonne of water apply 0.5 kg (or more) of hydrated Hi Concentration Aqua Product per 1,000 square meters of encierro; for animals held at a density of about 50 to 250 per tonne of water apply 0.1 kg of hydrated Hi Concentration Aqua Product per 1,000 square meters. The Low Concentrated Aqua Product is used for providing a greater organic fertilizer function in large-ponds systems where encierros are not used and incoming water quality is low in nutrients requiring heavy fertilization.

If possible, use an aerator in the encierro; however, if this is not practical, then water exchange should be used to keep dissolved oxygen above 4 ppm. When a large exchange is made, add Aqua Product after exchanging the water.

When growth rates slow down, the encierro should be expanded to a larger portion of the pond area or the juvenile shrimp should be released. Aqua Product may be applied to the whole pond 3 days before the juveniles are released from the encierro. Add 1 kg/ha of Hi Concentration Aqua Product or 10 kg/ha of Low Concentration Aqua Product to the whole pond 2-3 days before releasing the juveniles, and as needed during the crop.

Response to Presence of Luminous *Vibrio*

A farmer may respond to presence of luminous *Vibrio* by managing the bacterial community composition to keep bacterial species balanced in favor of beneficial strains. The present invention provides a range of specially selected strains of microbial technology microbes that compete with and inhibit *Vibrio* in ponds and hatchery tanks and/or bioactive compounds such as quorum sensing inhibitor compounds. When used with the total management system according to the present invention, including phytoplankton management, *Vibrio* numbers typically can be controlled at less than about 1000 to 500/mL in intensive shrimp ponds. Some of these microbial technology bacteria (*Bacillus* species) are selected for their competitive ability to remove the food of other heterotrophs such as *Vibrio*, or their protective slime coats. Others are selected for their direct inhibitory effects on *Vibrio harveyi* (and certain other potentially pathogenic *Vibrio* species) through specific antibiotic secretion.

Algae can be controlled by manipulating nutrient ratios through controlled feeding, and fertilizer additions, recycling of pond water and using bacteria according to the present invention to compete with algae for an essential nutrients. The following section describes Hatchery Product application guidelines, according to the present invention.

Preparation of Hatchery Product Suspension

Prepare a suspension of 2 g/L for use in hatchery tank water and another of 100 g/L for mixing with hatchery feed: (i) heat 200 mL fresh water to 65° C.; (ii) add the 2 or 100 g of the Hatchery. Product powder and mix well; (iii) stand for 5 minutes; (iv) add 800 mL sterilized seawater at ambient temperature (about 25° C.); (v) cover and stand for about 12 hours at 30-35° C.; (vi) apply suspension to hatchery tank water daily at about 500 ppm and to feed at 200 mL per kilogram; (vii) store extra suspension for a further 12 hours maximum for mixing with feed; and (viii) store and refrigerate suspensions.

Application

Monitor *Vibrio* with TCBS medium in tanks and larvae. If numbers are too high, especially luminous *Vibrio*, double the dose of the Hatchery Product suspension.

Feed Application:

Apply the Hatchery Product suspension (100 g/L) to feed for all broodstock and larvae at 200 mL per kg feed by mixing suspension with feed immediately before feeding. The feed may be stored chilled, but not frozen, after mixing with the Hatchery Product suspension. The Hatchery Product suspension should be mixed directly with all artificial feed for larvae at 200 mL per kg feed by mixing suspension until it is absorbed by the feed immediately before feeding.

Artemia Tanks

Apply the Hatchery Product suspension (2 g/L) to Artemia cultures during cyst hatching at 40 L per tonne of water and add daily to the Artemia tanks as needed. Check total and luminous *Vibrio* numbers at 24 hours after hatching; if *Vibrio* numbers are too high use increase doses.

Spawning Tanks:

Mix 500 mL Hatchery Product suspension (2 g/L) per 1 tonne (1000 L) of water in spawner holding tanks while eggs are released. Remove all faeces of spawners from tanks.

Larval Rearing Tanks

N3 to Z3 stages: add 500 mL Hatchery Product suspension per tonne of water on the first day, then 250 mL until water exchange starts. Note that the actual volumes and dosages may be varied from time to time depending on product composition or varied in accordance with the particular microbial community of a hatchery of the end user 108 to 110.

According to results of the microbial technology according to the present invention, in Panama, as described with respect to Table 5 below, two farms, with both of the farms following guidelines and using products according to the present invention in some or all of their production ponds, reported good survival in the range of 60-90% survival, while many other farms in the country experienced heavy mortality, 5-25% survival, due to White Spot Virus and pathogenic bacteria by day 30 to 40 of culture. In Table 5, the exemplary test data showed a first profitable shrimp production in over 18 months in the two farms in Panama, "La Fe" and "Anton" farms. The results are from a first harvest during March-June 2000 in ponds 1-10 (La Fe) and P3 (Anton) using "best practice" recommendation with Aqua Product Encierro and Feed Product according to the present invention. Profits were realized for the first time in over 18 moths since White Spot Virus hit Panama in 1999. Shrimp in ponds 1-10 and in P3 and P4 were from Panamanian stocks, which tested positive for White Spot Virus (by PCR, polymerase chain reaction test). Ponds 1-3 were Controls at La Fe originally using a treatment of brown sugar, which then were switched to the Aqua Product Encierro and Aqua Product Feed according to the present invention at about day 20 of culture and before any signs of disease were observed. Ponds P2 and P4 were brown sugar Controls, abandoned after disease symptoms appeared at about 45 days of culture. In Pond P1 the Aqua Product Encierro and Aqua Product Feed were not used in the manner used in Pond P3 or ponds 1-10. During this trial most shrimp farmers in Panama continued to experience heavy mortalities by about 40 days of culture with heavy financial losses to the industry. Thus these results showed that when the microbial technology described in this invention was used, it was possible for farmers to produce crops successfully.

TABLE 5

Exemplary test data for Panama.

| Pond | Area (ha) | Stock. Dens. (per m²) | Survival (%) | Harvest (kg/ha) | Profit ($/ha) | Test Method |
|---|---|---|---|---|---|---|
| 1[a] | 1.2 | 10.1 | 92 | 1033 | $4,181 | Encierro; Panamanian larvae (seedstock) |
| 2[a] | 3.9 | 16.3 | 55 | 800 | $2,501 | Encierro; Panamanian larvae (seedstock) |
| 3[a] | 2.4 | 14.6 | 75 | 869 | $1,955 | Encierro; Panamanian larvae (seedstock) |
| 4[b] | 2.7 | 16.5 | 45 | 819 | $2,024 | Encierro Panamanian larvae (seedstock) |
| 5 | 2.8 | 15.8 | 75 | 781 | $1,186 | Encierro; Panamanian larvae (seedstock) |
| 6 | 2.7 | 15.4 | 86 | 1032 | $2,260 | Encierro Panamanian larvae (seedstock) |
| 7 | 2.6 | 17.0 | 59 | 778 | $1,480 | Encierro; Panamanian larvae (seedstock) |
| 8 | 5.2 | 13.7 | 70 | 693 | $1,685 | Encierro; Panamanian larvae (seedstock) |
| 9 | 5.1 | 15.8 | 60 | 634 | $1,015 | Encierro; Panamanian larvae (seedstock) |
| 10 | 1.9 | 16.6 | 67 | 739 | $ 641 | Encierro; Panamanian larvae (seedstock) |
| P1[c] | 1.0 | 15.8 | 53 | 597 | -$ 834 | Full Pond; SPF larvae (seedstock) |
| P2[d] | 2.9 | 13.6 | — | — | -$2,171 | Brown Sugar, abandoned day 45; SPF larvae (seedstock) |
| P3 | 4.9 | 16.8 | 63 | 843 | $1,783 | Encierro; Panamanian larvae (seedstock) |
| P4[d] | 6.0 | 16.7 | 64 | 643 | -$ 623 | Brown Sugar, abandoned day 45; Panamanian larvae (seedstock) |

[a]CONTROL ponds treated with brown sugar switched to Aqua Product-Encierro and Aqua Product Feed by day 20, before experiencing disease.
[b]Harvest lasted 3 days due to drainage problem in pond: on third day harvested 816 kg by manual cast net; survival artificially low due to drainage problem.
[c]Aqua Product Encierro not used, rather Aqua Product Full Pond used with SPF seedstock.
[d]CONTROL ponds treated with brown sugar switched to Aqua Product Encierro on day 45, after experiencing disease.

The following Table 6 contains results of commercial field trials performed between January and May 2001 in Machala Ecuador at shrimp farm Bravo Grande of Pesquera Bravito. Three (3) commercial ponds (total of 33.5 ha. stocked at 7.7 postlarval shrimp per m²) were used as controls where the standard technical management practices of the farm were employed; and three other test ponds (total of 31.5 ha. stocked at 7.5 postlarval shrimp per m²) were treated with the technology of the present invention including use of the microbial products. As shown in Table 6, the ponds that were managed according to the biocontrol program of the present invention had significantly greater production and Net Profit relative to the control ponds.

TABLE 6

Exemplary test data for Ecuador.

| Factor | Controls | Test | Difference |
|---|---|---|---|
| Production (lb/ha) | 950 | 1230 | 280 |
| Growth Rate (g/week) | 1.0 | 1.4 | 0.4 |
| Feed Conversion Ratio | 1.18 | 0.99 | -0.19 |
| Size at Harvest (g) | 16.8 | 18.8 | 2.0 |
| Days of Culture | 115 | 96 | -19 |
| Survival (%) | 34 | 40 | 6% |
| Product Expenses ($/ha/crop) | 0 | $ 295 | $295 |
| Net Profit ($/ha) | $862 | $1,855 | $993 |

Table 7, shows results of the microbial technology according to the present invention, in hatcheries.

TABLE 7

Percent Survival of Larval *L. vannamei* grown in a commercial shrimp hatchery tanks during outbreak of the Zoea Syndrome.

| CONTROL | HATCHERY PRODUCT |
|---|---|
| 51 | 59 |
| 50 | 78 |
| 15 | 79 |
| 43 | 83 |
| 83 | 95 |
| Average: 48.4 | Average: 78.8 |

Analysis of Microbial Samples Taken from End User Locations

The present invention includes maintaining bacterial cultures on agar slopes, in frozen storage or as described in [21] or [22]. For screening the inhibitory effect of probiotic bacteria strains of the present invention on microbial samples taken from end user 108 to 110 locations where disease is present, a line is streaked across the center of a petri dish prepared with tryptone soy agar in 1%-6% NaCl. Incubation is performed at 28-32° C. for 2 days, then the potential pathogenic bacterial strain (e.g., *Vibrio* strain to be tested) is cross streaked at right angles to the line of probiotic bacterial streaked previously (prepared as noted below). Incubation is then performed for a further 3 days. Clear zones (i.e., no growth of *Vibrio*) close to the probiotic bacterial strain (e.g., *Bacillus* sp.) indicate inhibition of the potential pathogen by the probiotic strain.

Pathogenic *Vibrio* strains: Grow these in nutrient broth in 2% NaCl overnight, then transfer 0.1 mL to 10 mL of sterile 2% NaCl solution before plating onto agar with *Bacillus*. Streak 5-10 μL with a loop. Tests for seeking and selecting probiotic bacteria active against other pathogenic bacteria, whether marine or freshwater in origin, may be conducted in a similar manner.

Figure 8:
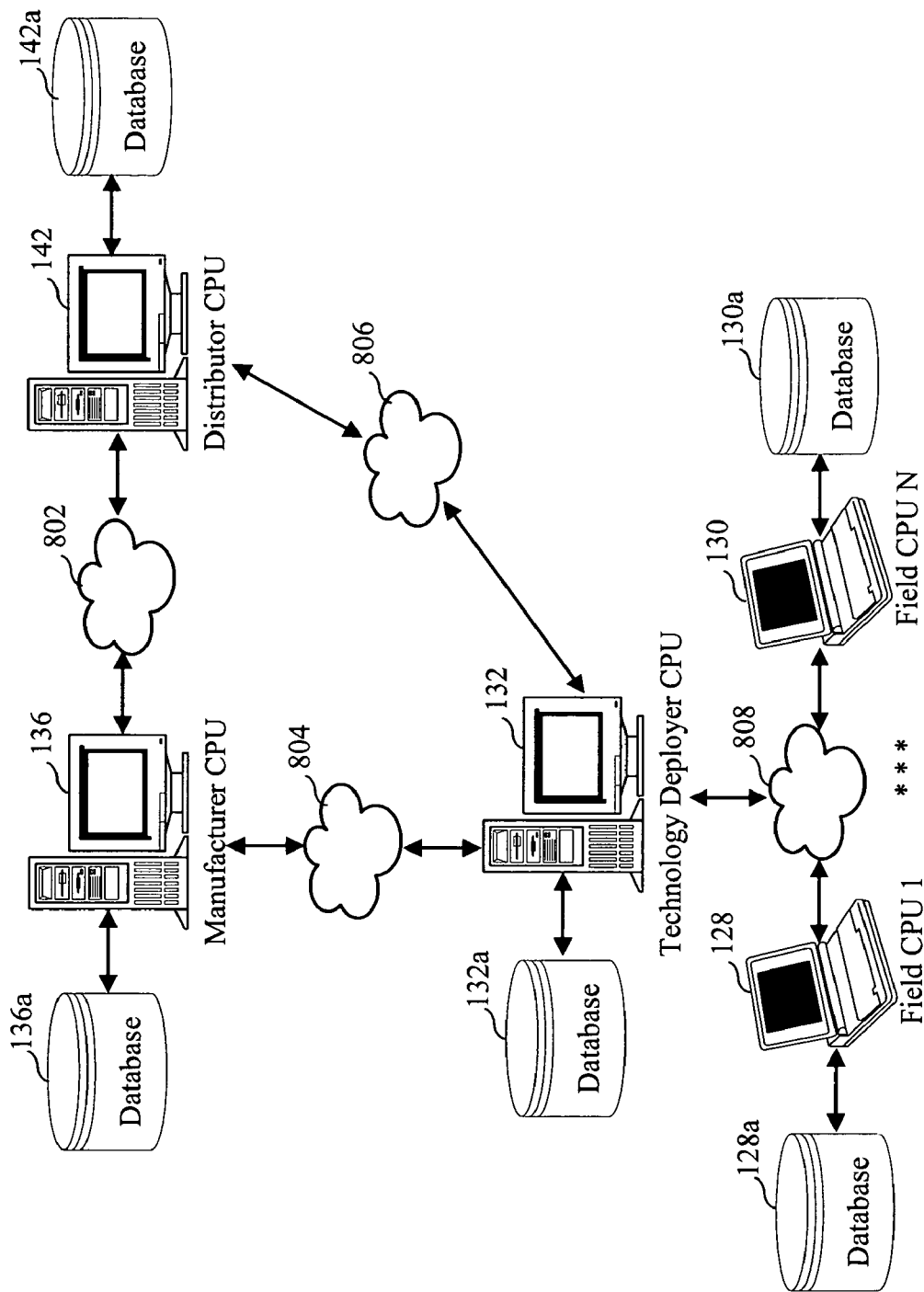
FIG. 8 is a detailed network system diagram of the system of FIG. 1, according to the present invention.

FIG. 8 illustrates an overall network system diagram, according to the present invention. In FIG. 8, the system includes the field computers 128 to 130, the technology deployment computer 132, the manufacturer computer 136, the distributor computer 142 and respective databases 128a, 130a, 132a, 136a and 142a. The computers 128, 130, 132, 136 and 142 are coupled via respective communications networks 802, 804, 806 and 808, as shown in FIG. 8. The communications networks 802, 804, 806 and 808 may be implemented via one or more communications networks (e.g., the Internet, an Intranet and/or a combination of the Internet and Intranets) based on data security and other concerns, as will be appreciated by those skilled in the relevant art(s). In a preferred embodiment of the present invention, the communications network(s) preferably use electrical, electromagnetic, or optical signals that carry digital data streams.

It is to be understood that the system in FIG. 8 is for exemplary purposes only, as many variations of the specific hardware used to implement the present invention will be readily apparent to one having ordinary skill in the art. For example, the functionality of the various computers 128, 130, 132, 136 and 142 may be implemented via one or more programmed computers. To implement such variations as well as other variations, a single computer (e.g., the computer system 901 of FIG. 9) may be programmed to perform the special purpose functions of the various computers shown in FIG. 8. On the other hand, two or more programmed computers may be substituted for any one of the computers 128, 130, 132, 136 and 142 shown in FIG. 8. Principles and advantages of distributed processing, such as redundancy and replication, may also be implemented as desired to increase the robustness and performance of the system, for example.

Data structures are used to store the various data from the aforementioned discussions and include fields for storing same. The present invention thus stores information relating to various processes described herein. This information is stored in one or more memories such as a hard disk, optical disk, magneto-optical disk, and/or RAM, for example. One or more databases, such as the respective databases 128, 130, 132, 136 and 142 shown in FIG. 8, may store the information used to implement the present invention. The databases are organized using data structures (e.g., records, tables, arrays, fields, graphs, trees, and/or lists) contained in one or more memories, such as the memories listed above or any of the storage devices listed below in the discussion of FIG. 9, for example.

All or a portion of the invention may be conveniently implemented using conventional general purpose computers or microprocessors programmed according to the teachings of the present invention, as will be apparent to those skilled in the computer art. Appropriate software can be readily prepared by programmers of ordinary skill based on the teachings of the present disclosure, as will be apparent to those skilled in the software art.

Figure 9:
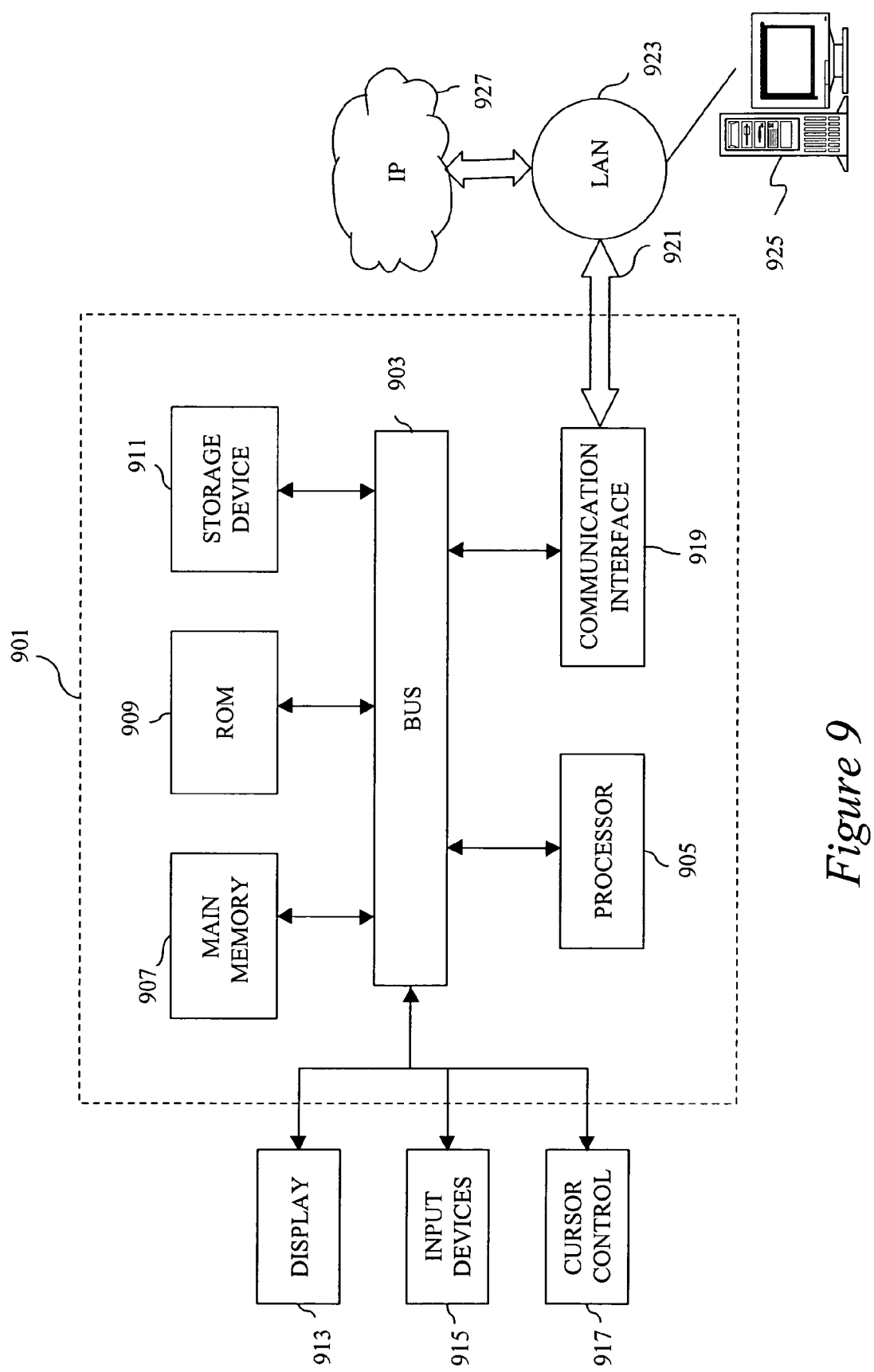
FIG. 9 is an exemplary computer system that may be programmed to perform one or more of the processes of the present invention.

FIG. 9 illustrates a computer system 901 upon which an embodiment of the present invention may be implemented. Computer system 901 includes a bus 903 or other communication mechanism for communicating information, and a processor 905 coupled with bus 903 for processing the information. Computer system 901 also includes a main memory 907, such as a random access memory (RAM) or other dynamic storage device (e.g., dynamic RAM (DRAM), static RAM (SRAM), synchronous DRAM (SDRAM), flash RAM), coupled to bus 903 for storing information and instructions to be executed by processor 905. In addition, main memory 907 may be used for storing temporary variables or other intermediate information during execution of instructions to be executed by processor 905. Computer system 901 further includes a read only memory (ROM) 909 or other static storage device (e.g., programmable ROM (PROM), erasable PROM (EPROM), and electrically erasable PROM (EEPROM)) coupled to bus 903 for storing static information and instructions for processor 905. A storage device 911, such as a magnetic disk or optical disk, is provided and coupled to bus 903 for storing information and instructions.

The computer system 901 may also include special purpose logic devices (e.g., application specific integrated circuits (ASICs)) or configurable logic devices (e.g., generic array of logic (GAL) or re-programmable field programmable gate arrays (FPGAs)). Other removable media devices (e.g., a compact disc, a tape, and a removable magneto-optical media) or fixed, high-density media drives may be added to the computer system 901 using an appropriate device bus (e.g., a small computer system interface (SCSI) bus, an enhanced integrated device electronics (IDE) bus, or an ultra-direct memory access (DMA) bus). The computer system 901 may additionally include a compact disc reader, a compact disc reader-writer unit, or a compact disc jukebox, each of which may be connected to the same device bus or another device bus.

Computer system 901 may be coupled via bus 903 to a display 913, such as a cathode ray tube (CRT), for displaying information to a computer user. The display 913 may be controlled by a display or graphics card. The computer system includes input devices, such as a keyboard 915 and a cursor control 917, for communicating information and command selections to processor 905. The cursor control 917, for example, is a mouse, a trackball, or cursor direction keys for communicating direction information and command selections to processor 905 and for controlling cursor movement on the display 913. In addition, a printer may provide printed listings of the data structures/information or any other data stored and/or generated by the computer system 901.

The computer system 901 performs a portion or all of the processing steps of the invention in response to processor 905 executing one or more sequences of one or more instructions contained in a memory, such as the main memory 907. Such instructions may be read into the main memory 907 from another computer readable medium, such as storage device 911. One or more processors in a multi-processing arrangement may also be employed to execute the sequences of instructions contained in main memory 907. In alternative embodiments, hard-wired circuitry may be used in place of or in combination with software instructions. Thus, embodiments are not limited to any specific combination of hardware circuitry and software.

As stated above, the system 901 includes at least one computer readable medium or memory programmed according to the teachings of the invention and for containing data structures, tables, records, or other data described herein. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling the computer system 901, for driving a device or devices for implementing the invention, and for enabling the computer system 901 to interact with a human user (e.g., a researcher, a manufacturer, a distributor, a filed technician, an end user, etc.). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpreted or executable code mechanism, including but not limited to scripts, interpreters, dynamic link libraries, Java classes, and complete executable programs. Moreover, parts of the processing of the present invention may be distributed for better performance, reliability, and/or cost.

The term "computer readable medium" as used herein refers to any medium that participates in providing instructions to processor 905 for execution. A computer readable medium may take many forms, including but not limited to, non-volatile media, volatile media, and transmission media. Non-volatile media includes, for example, optical, magnetic disks, and magneto-optical disks, such as storage device 911. Volatile media includes dynamic memory, such as main memory 907. Transmission media includes coaxial cables, copper wire and fiber optics, including the wires that comprise bus 903. Transmission media also may also take the form of acoustic or light waves, such as those generated during radio wave and infrared data communications.

Common forms of computer readable media include, for example, hard disks, floppy disks, tape, magneto-optical disks, PROMs (EPROM, EEPROM, Flash EPROM), DRAM, SRAM, SDRAM, or any other magnetic medium, compact disks (e.g., CD-ROM), or any other optical medium, punch cards, paper tape, or other physical medium with patterns of holes, a carrier wave (described below), or any other medium from which a computer can read.

Various forms of computer readable media may be involved in carrying out one or more sequences of one or more instructions to processor 905 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to computer system 901 may receive the data on the telephone line and use an infrared transmitter to convert the data to an infrared signal. An infrared detector coupled to bus 903 can receive the data carried in the infrared signal and place the data on bus 903. Bus 903 carries the data to main memory 907, from which processor 905 retrieves and executes the instructions. The instructions received by main memory 907 may optionally be stored on storage device 911 either before or after execution by processor 905.

Computer system 901 also includes a communication interface 919 coupled to bus 903. Communication interface 919 provides a two-way data communication coupling to a network link 921 that may be connected to, for example, a local network 923. For example, communication interface 919 may be a network interface card to attach to any packet switched local area network (LAN). As another example, communication interface 919 may be an asymmetrical digital subscriber line (ADSL) card, an integrated services digital network (ISDN) card or a modem to provide a data communication connection to a corresponding type of telephone line. Wireless links may also be implemented. In any such implementation, communication interface 919 sends and receives electrical, electromagnetic or optical signals that carry digital data streams representing various types of information.

Network link 921 typically provides data communication through one or more networks to other data devices. For example, network link 921 may provide a connection to a computer 925 through local network 923 (e.g., a LAN) or through equipment operated by a service provider, which provides communication services through a communications network 927. In preferred embodiments, local network 923 and communications network 927 preferably use electrical, electromagnetic, or optical signals that carry digital data streams. The signals through the various networks and the signals on network link 921 and through communication interface 919, which carry the digital data to and from computer system 901, are exemplary forms of carrier waves transporting the information. Computer system 901 can transmit notifications and receive data, including program code, through the network(s), network link 921 and communication interface 919.

Recapitulating, with multiple pathogens now present in the environment: pathogenic *Vibrios*, White Spot Virus, Taura Syndrome Virus, Yellow Head Virus, NHP and others—the methods of aquaculture have changed forever. In this respect, the present invention includes recognition that simply adding beneficial bacteria to aquaculture systems typically does not necessarily provide a solution to disease. The addition of bacteria must be integrated into a wider application of principles of microbial ecology [10, 12-14].

The present invention further includes recognition that pond management advice, as related to economics of production, is affected by disease and level of biocontrol designed for the end user: For example, if farmer A wants 95% survival of 20 gram shrimp harvested at 6000 kg per hectare, costs will be much higher, as will yields, and a very different biocontrol program will be designed than for a farmer B who wants 750 kg/ha of 14 gram shrimp and can do well for his goals with 45% survival. In this case, farmer A can spend as much as $1200/ha on biocontrol, while farmer B can spend as much as $350/ha on biocontrol.

In the above respect, the present invention provides a unique combination of technology, experience, reputation and know-how that help to control disease in aquaculture by adapting to the new set of conditions resulting from the way microbes are evolving.

Although the present invention is described in terms of disease control for aquaculture applications, food processing applications, commercial aquaria applications, hobby aquaria applications, etc., the present invention may be practiced to control disease in other applications, such as in terrestrial farm animal production, etc., as will be appreciated by those skilled in the relevant art(s).

Although the present invention is described in terms of gathering samples and/or data using laboratory techniques, the present invention may be practiced by collecting samples and/or data using bio-chips and bio-sensors as taught in, for example, [23-25], as will be appreciated by those skilled in the relevant art(s).

Numerous modifications and variations of the present invention are possible in light of the above teachings. It is therefore to be understood that within the scope of the appended claims, the invention may be practiced otherwise than as specifically described herein.

LIST OF REFERENCES

[1] Food and Agriculture Organization (FAO), 1996. The State of the World Fisheries and Aquaculture, SOFIA

[2] Moriarty, D. J. W., J. P. E. C. Darlington, I. G., Dunn, C. M. Moriarty and M. P. Tevlin. 1973. Feeding and grazing in Lake George, Uganda Proc. R. Soc. Lond. 184: 299-319.

[3] Moriarty, D. J. W. 1986. Bacterial productivity in ponds used for culture of penaeid prawns. Microbial Ecology. 12: 259-270.

[4] Moriarty, D. J. W. and R. S. V. Pullin, editors. 1987. Detritus and microbial ecology in aquaculture. ICLARM Conference Proceedings 13: 385p. International Centre for Living Aquatic Resources Management, Manila Philippines.

[5] Moriarty, D. J. W. 1990. Interactions of microorganisms and aquatic animals, particularly the nutritional role of the gut flora. pp. 217-222. In: R. Lésel (Ed.), Microbiology in Poecilotherms. Elsevier Science Publishers, B. V. (Biomedical Division).

[6] Allan, G. L., Moriarty, D. J. W., Maguire, G. B. 1995. Effects of pond preparation and feeding rate on production of Penaeus monodon Fabricius, water quality, bacteria and benthos in model farming ponds. Aquaculture.130: 329-349.

[7] Moriarty, D. J. W. and R. T., Bell. 1993 Bacterial growth and starvation in the sea and lakes. In: S. Kjelleberg ed. Starvation of Bacteria. Plenum Press. 25-53.

[8] Moriarty, D. J. W. 1996 Microbial Biotechnology: a Key Ingredient for Sustainable Aquaculture. Infofish International. July/August pp 29-33.

[9] Moriarty, D. J. W. 1997. The role of micro-organisms in aquaculture ponds. Aquaculture 151: 333-349.

[10] Moriarty, D. J. W. 1997. Probiotics and Biotechnology in Aquaculture. Sustainable Aquaculture: proceedings of the INFOFISH-AQUATECH 96: International Conference on Aquaculture, Kuala Lumpur, Malaysia. Infofish, 1997.

[11] Moriarty, D. J. W., Bianchi, M. and Talbot, V. 1997. Bacterial productivity and organic matter flux in the Southern Ocean and in the Antarctic Intermediate water and Mode waters of the Indian Ocean. Deep-Sea Research II, 44: 1005-1015.

[12] Moriarty, D. J. W. 1998. Microbial Ecology: the Key to Controlling Virus and Bacterial Disease in Aquaculture. Microbiology Australia. 19: 22-27.

[13] Moriarty, D. J. W2000. Disease Control in Shrimp Aquaculture with Probiotic Bacteria. In: Microbial Biosystems: New Frontiers. Proceedings of the 8th International Symposium on Microbial Ecology. Bell, C R, Brylinski, M., Johnson-Green, P. (eds). Atlantic Society for Microbial Ecology, Halifax, Canada.

[14] Moriarty, D. J. W. 1998. Control of luminous Vibrio species in aquaculture ponds. Aquaculture. 164: 351-358.

[15] Moriarty, D. J. W., B. Withyachunmnarnkul, P Pratanpipat and C Nitimethachoke. In press. Managing Microbial Disease in Aquaculture with Probiotic Bacteria: Biotechnology for Sustainable Aquaculture. J. Marine Biotechnology.

[16] Villamar, D. F. and A. L. Lawrence. Effects of dietary protein quality on glutamate dehydrogenase activity in postlarval Shrimp Penaeus vannamei Boone. [An oral presentation at the conference of the World Aquaculture Society 1992].

[17] Villamar, D. F. and C. J. Langdon. 1993. Delivery of dietary components to larval shrimp (Penaeus vannamei) by means of complex microcapsules. Marine Biology, 115(4): 635-642.

[18] Villamar, D. F. 1993. Alimentos balanceados de alta calidad para el cultivo del camarón: alimento balanceado completo. Seminario Tecnico de Nutricion y Cultivo Semiintensivo de Camarón, ANDAH, Choluteca, Honduras, 5 Febrero 1993. [High-quality balanced feed for shrimp culture: complete feed; an oral presentation to the National Association of Honduran Aquaculturists]

[19] Villamar, D. F. 1997. Alimento Liquido: Una Nueva Tecnologia Para el Cultivo de Camarón Larvario. IV Simposio Centroamericano de Acuacultura, Cultivo Sostenible de Camarón y Tilapia. Tegucigalpa Honduras 22-24 de abril de 1997. [Liquid feed: a new technology for the culture of larval shrimp; an oral presentation at the IV Central American Aquaculture Symposium.]

[20] Villamar, D. F. 1998. Invited Speaker: The International Market and Global Needs in Aquaculture, presented at "Scientific Advances in Animal Nutrition: Promise for the Next Century," a symposium held in celebration of the 70th Anniversary of the National Research Council's Committee on Animal Nutrition, Dec. 9, 1998, at the National Academy of Sciences, 2101 Constitution Ave. N.W. Washington, D.C.

[21] Bergey's Manual of Determinative Bacteriology, Buchanan, R. E. and Gibbons, N. E. (eds) 8th edition. Baltimore: Williams and Wilkins. (1974), page 1109.

[22] Norris, J. R. et al. (1981) The Genera Bacillus and Sporobacillus. In The Prokaryotes Starr, M. P et al. Berlin: Springer-Verlag.

[23] Yamaguchi, et al., U.S. Pat. No. 5,180,494, entitled "Method of controlling waste water treatment by anaerobic fermentation," issue date: Jan. 19, 1993.

[24] Rowe, et al., "Array biosensor for simultaneous identification of bacterial, viral, and protein analytes," Anal Chem. Sep. 1, 1999;71(17):3846-52; PMID: 10489530; UI: 99419372.

[25] O'Brien, et al, "The development of immunoassays to four biological threat agents in a bidiffractive grating biosensor," Biosens Bioelectron. 2000 January;14(10-11):815-28; [MEDLINE record in process]; PMID: 10945456; UI: 20399553.

[26] Kjelleberg et al, Patent Number WO 9629392, entitled "Methods for Microbial Regulation," publication date: Sep. 26, 1996.

[27] Manefield, M, Harris, L, Rice, S A, Nys, R de, Kjelleberg, S. 2000. Inhibition of Luminescence and Virulence in the Black Tiger Prawn (Penaeus monodon) Pathogen Vibrio harveyi by Intercellular Signal Antagonists. Applied and Environmental Microbiology. 66: 2079-2084.

[28] Murray, G. E., Tobin, R. S., Junkins, B., Kushner, D. J. (1984) Effect of chlorination on antibiotic resistance profiles of sewage-related bacteria Applied and Environmental Microbiology. 48: 73-77.

[29] Moken, M C, McMurray, L M, Levy, S B. 1997. Selection of multiple-antibiotic resistant (Mar) mutants of Escherichia coli by using the disinfectant pine oil: roles of the mar and acrAB loci. Antimicrobial Agents and Chemotherapy 41: 2770-2772.

[30] Nikolich, M. P., Hong, G., Shoemaker, N. B., Salyers, A. A. (1994) Evidence for Natural Horizontal Transfer of tetQ between Bacteria that normally Colonise Humans and Bacteria that Normally Colonise Livestock Applied and Environmental Microbiology. 60: 3255-3260.

[31] Kruse, H., Sørum, H. (1994). Transfer of Multiple Drug Resistance Plasmids between Bacteria of Diverse Origins in Natural Environments. Applied and Environmental Microbiology. 60: 4015-4021.

[32] Feinman S E. 1998. Antibiotics in animal Feed-drug resistance revisited. ASM News. 64: 24-30.

[33] Austin, B et al 1995. A probiotic strain of Vibrio alginolyticus effective in the reducing diseases caused by Aeromonas salmonicida, Vibrio anguillarum and Vibrio ordalli.

[34] Vandenberghe J et al 1999. Vibrios Associated with Litopenaeus vannamei Larvae, Postlarvae, Broodstock, and Hatchery Probionts. Applied and Environmental Microbiology. 65; 2592-2597.

[35] Ziebuhr W, Ohlsen K, Karch H, Korhonen T, Hacker J 1999. Evolution of bacterial pathogenesis. Cellular And Molecular Life Sciences 56: 719-728.

What is claimed is:

1. A process for controlling disease in aquatic animals at an end user location, comprising:
    (a) testing a range of candidates including at least one of: (i) *Bacillus* species, (ii) *Bacillus* strains, (iii) species of beneficial bacteria (iv) strains of beneficial bacteria and (v) strains of beneficial bacterial viruses, against samples including at least one of pathogenic *Vibrio*, Gram negative pathogenic bacteria and Gram positive pathogenic bacteria taken from an end user location;
    performing the step of selecting one or more of the candidates that inhibit and attack at least one of the samples by at least one of in situ antibiotic production, competitive exclusion, and production of enzymes that degrade quorum sensing molecules,
    (b) testing a range of quorum sensing inhibitor compounds against the samples; and
    (c) performing the steps (a) and (b) for the end user location, including one of a country, major region and individual end user location, to determine microbial strain composition based on the selected candidate and/or quorum sensing inhibitor compounds and the tested range of quorum sensing inhibitor compounds to formulate a product and target microbial technology for use in bio-control of disease specific to the end user location.

2. The process of claim 1, further comprising:
    receiving at least one of physico-chemical data, biological data and management data from the end user location; and
    providing at least one of a general bio-control program, a customized bio-control program, a general bio-control product and a customized bio-control product to manage disease at the end user location based on at least one of the received physicochemical data, biological data and management data and the samples.

3. The process of claim 2, wherein the step of providing general and customized bio-control programs includes providing at least one of pond management advice, pond bottom preparation advice, fertilization advice, stocking advice, water management advice, aeration advice, nutrition advice, feeding advice, hatchery culture advice, grow-out production advice, advise on the application and dose rates of microbial technology products to water and feed, training services and management advice as related to economics of production, specific to the end user location.

4. A computer-readable medium carrying one or more sequences of one or more instructions for controlling disease in aquatic animals at an end user location, the one or more sequences of one or more instructions including instructions which, when executed by one or more processors, cause the one or more processors to perform the steps of:
    (a) testing a range of candidates including at least one of: (i) *Bacillus* species, (ii) *Bacillus* strains, (iii) species of beneficial bacteria (iv) strains of beneficial bacteria and (v) strains of beneficial bacterial viruses, against samples including at least one of pathogenic *Vibrio*, Gram negative pathogenic bacteria and Gram positive pathogenic bacteria taken from an end user location;
    performing the step of selecting one or more of the candidates that inhibit and attack at least one of the samples by at least one of in situ antibiotic production, competitive exclusion, and production of enzymes that degrade quorum sensing molecules,
    (b) testing a range of quorum sensing inhibitor compounds against the samples; and
    (c) performing the steps (a) and (b) for the end user location, including one of a country, major region and individual end user location, to determine microbial strain composition based on the selected candidate and/or quorum sensing inhibitor compounds and the tested range of quorum sensing inhibitor compounds to formulate a product and target microbial technology for use in bio-control of disease specific to the end user location.

5. The computer-readable medium of claim 4, further comprising:
    receiving at least one of physicochemical data, biological data and management data from the end user location; and
    providing at least one of a general bio-control program, a customized bio-control program, a general bio-control product and a customized bio-control product to manage disease at the end user location based on at least one of the received physicochemical data, biological data and management data and the samples.

6. The computer-readable medium of claim 5, wherein the step of providing general and customized bio-control programs includes providing at least one of pond management advice, pond bottom preparation advice, fertilization advice, stocking advice, water management advice, aeration advice, nutrition advice, feeding advice, hatchery culture advice, grow-out production advice, advise on application and dose rates of microbial technology products to water and feed, training services and management advice as related to economics of production, specific to the end user location.

7. A system for controlling disease in aquatic animals at an end user location, comprising:
    (a) means for testing a range of candidates including at least one of: (i) *Bacillus* species, (ii) *Bacillus* strains, (iii) species of beneficial bacteria (iv) strains of beneficial bacteria and (v) strains of beneficial bacterial viruses, against samples including at least one of pathogenic *Vibrio*, Gram negative pathogenic bacteria and Gram positive pathogenic bacteria taken from an end user location;
    means for selecting one or more of the candidates that inhibit and attack at least one of the samples by at least one of in situ antibiotic production, competitive exclusion, and production of enzymes that degrade quorum sensing molecules,
    (b) means for testing a range of quorum sensing inhibitor compounds against the samples; and
    (c) means for performing (a) and (b) for the end user location, including one of a country, major region and individual end user location, to determine microbial strain composition based on the selected candidate and/or quorum sensing inhibitor compounds and the tested range of quorum sensing inhibitor compounds to formulate a product and target microbial technology for use in bio-control of disease specific to the end user location.

8. The system of claim 7, further comprising:
    means for receiving at least one of physicochemical data, biological data and management data from the end user location; and
    means for providing at least one of a general bio-control program, a customized bio-control program, a general bio-control product and a customized bio-control product to manage disease at the end user location based on at least one of the received physicochemical data, biological data and management data and the samples.

9. The system of claim 8, wherein the means for providing general and customized bio-control programs includes means for providing at least one of pond management advice, pond bottom preparation advice, fertilization advice, stocking advice, water management advice, aeration advice, nutrition advice, feeding advice, hatchery culture advice, grow-out production advice, advise on the application and dose rates of microbial technology products to water and feed, training services and management advice as related to economics of production, specific to the end user location.

10. A system configured to control disease in aquatic animals at an end user location, comprising:
(a) a technology deployer configured to test a range of candidates including at least one of: (i) *Bacillus* species, (ii) *Bacillus* strains, (iii) species of beneficial bacteria (iv) strains of beneficial bacteria and (v) strains of beneficial bacterial viruses, against samples including at least one of pathogenic *Vibrio*, Gram negative pathogenic bacteria and Gram positive pathogenic bacteria taken from an end user location;
the technology deployer further configured to perform the step of selecting one or more of the candidates that inhibit and attack at least one of the samples by direct inhibition of at least one of in situ antibiotic production, competitive exclusion, and production of enzymes that degrade quorum sensing molecules, and
(b) testing a range of quorum sensing inhibitor compounds against the samples,
wherein the technology deployer is further configured to perform (a) and (b) at the end user location, including one of a country, major region and individual end user location, to determine microbial strain composition based on the selected candidate and/or quorum sensing inhibitor compounds and the tested range of quorum sensing inhibitor compounds to formulate a product and target microbial technology for use in bio-control of disease specific to the end user location.

11. The system of claim 10, wherein the technology deployer is further configured to receive at least one of physicochemical data, biological data and management data from the end user location; and
the technology deployer is further configured to provide at least one of a general bio-control program, a customized bio-control program, a general bio-control product and a customized bio-control product to manage disease at the end user location based on at least one of the received physicochemical data, biological data and management data and the samples.

12. The system of claim 11, wherein the general and customized bio-control programs include at least one of pond management advice, pond bottom preparation advice, fertilization advice, stocking advice, water management advice, aeration advice, nutrition advice, feeding advice, hatchery culture advice, grow-out production advice, advise on the application and dose rates of microbial technology products to water and feed, training services and management advice as related to economics of production, specific to the end user location.

* * * * *